United States Patent
Ie et al.

(10) Patent No.: US 10,793,584 B2
(45) Date of Patent: Oct. 6, 2020

(54) NAPHTHOBISCHALCOGENADIAZOLE DERIVATIVE AND PRODUCTION METHOD THEREFOR

(71) Applicants: OSAKA UNIVERSITY, Osaka (JP); ISHIHARA SANGYO KAISHA, LTD., Osaka (JP)

(72) Inventors: Yutaka Ie, Osaka (JP); Yoshio Aso, Osaka (JP); Takuji Seo, Osaka (JP); Taichi Moriyama, Osaka (JP)

(73) Assignees: Osaka University, Osaka (JP); Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 16/473,886

(22) PCT Filed: Oct. 13, 2017

(86) PCT No.: PCT/JP2017/037201
§ 371 (c)(1),
(2) Date: Jun. 26, 2019

(87) PCT Pub. No.: WO2018/123207
PCT Pub. Date: Jul. 5, 2018

(65) Prior Publication Data
US 2019/0337966 A1    Nov. 7, 2019

(30) Foreign Application Priority Data
Dec. 27, 2016   (JP) .................................. 2016-254341

(51) Int. Cl.
C07D 513/04    (2006.01)
C07D 517/04    (2006.01)

(52) U.S. Cl.
CPC .................................. C07D 513/04 (2013.01)

(58) Field of Classification Search
CPC .............................. C07D 513/04; C07D 517/04
See application file for complete search history.

(56) References Cited

U.S. PATENT DOCUMENTS

| | | | |
|---|---|---|---|
| 8,735,536 B2 | 5/2014 | Quinn et al. | |
| 2012/0227812 A1 | 9/2012 | Quinn et al. | |
| 2014/0163188 A1 | 6/2014 | Osaka et al. | |
| 2014/0319509 A1 | 10/2014 | Hattori et al. | |

FOREIGN PATENT DOCUMENTS

| | | | | |
|---|---|---|---|---|
| JP | 2000-282024 A | * | 10/2000 | ............. C09K 11/06 |
| JP | 2000-282024 A |   | 10/2000 | |
| JP | 2013-131716 A |   | 7/2013 | |
| JP | 2014-009163 A | * | 1/2014 | ........... C07D 513/04 |
| JP | 2014-053383 A | * | 3/2014 | ............. H01L 51/42 |
| JP | 2014-053383 A |   | 3/2014 | |
| WO | 2013/015298 A1 |   | 1/2013 | |
| WO | 2013/065573 A1 |   | 5/2013 | |
| WO | 2013/135339 A2 |   | 9/2013 | |
| WO | 2014/178415 A1 |   | 11/2014 | |
| WO | 2014/202184 A1 |   | 12/2014 | |
| WO | 2015/029432 A1 |   | 3/2015 | |
| WO | WO-2019/039369 A1 | * | 2/2019 | ............. C08G 61/12 |

OTHER PUBLICATIONS

An English translation of JP 2014-053383 A (Ito et al.), 2014. (Year: 2014).*
Wang et al., Journal of the American Chemical Society, 2011, 133, pp. 9638-9641. (Year: 2011).*
An English translation of WO 2019/039369 A1 (Osaka et al.), 2019 (Year: 2019).*
An English translation of JP 2000-282024 A (Tashiro et al.), 2000 (Year: 2000).*
An English translation of JP 2014-009163 (Kawashima et al.), 2014. (Year: 2014).*
Osaka, I. et al., "Naphthodithiophene-Naphthobisthiadiazole Copolymers for Solar Cells: Alkylation Drives the Polymer Backbone Flat and Promotes Efficiency", J. Am. Chem. Soc. 135, pp. 8834-8837 (2013).
Nakano, M. et al., "Naphthodithiophene Diimide (NDTI)-Based Semiconducting Copolymers: From Ambipolar to Unipolar n-Type Polymers", Macromolecules (2015) 48, pp. 576-584.
Wang, M. et al, "Donor-Acceptor Conjugated Polymer Based on Naphtho[1,2-c:5,6-c]bis[1,2,5]thiadiazole for High-Performance Polymer Solar Cells", J. Am. Chem. Soc. (2011) 133, 9638-9641.

(Continued)

Primary Examiner — Laura L Stockton
(74) Attorney, Agent, or Firm — Mintz Levin Cohn Ferris Glovsky and Popeo, P.C.; David G. Conlin; Joohee Lee

(57) ABSTRACT

In order to provide a naphthobischalcogenadiazole derivative that can be used as an intermediate for producing a naphthobischalcogenadiazole compound into which a fluorine atom has been introduced, the naphthobischalcogenadiazole derivative in accordance with an aspect of the present invention is represented by a formula (I):

[Chem. 1]

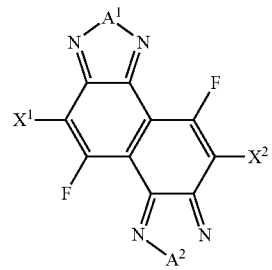

(I)

where each of $A^1$ and $A^2$ is independently an oxygen atom, a sulfur atom, a selenium atom, or a tellurium atom; and each of $X^1$ and $X^2$ is independently a hydrogen atom, a halogen atom, a boronic acid group, a boronic acid ester group, a boronic acid diaminonaphthalene amide group, an N-methyliminodiacetic acid boronate group, a trifluoroborate salt group, or a triolborate salt group.

15 Claims, No Drawings

(56) References Cited

OTHER PUBLICATIONS

International Search Report and Written Opinion for International Patent Application No. PCT/JP2017/037201, dated Nov. 21, 2017, 6 pages.
International Preliminary Report on Patentability for International Patent Application No. PCT/JP2017/037201, dated Jul. 2, 2019, 1 page.

* cited by examiner

NAPHTHOBISCHALCOGENADIAZOLE DERIVATIVE AND PRODUCTION METHOD THEREFOR

CROSS REFERENCE TO RELATED APPLICATION

The present application is a National Stage Entry of the International Patent Application No. PCT/JP2017/037201 filed Oct. 13, 2017, which also claims the benefit of priority of the Japanese Patent Application No. 2016-254341 filed Dec. 27, 2016.

TECHNICAL FIELD

The present invention relates to a naphthobischalcogenadiazole derivative into which a fluorine atom has been introduced and to a method for producing the naphthobischalcogenadiazole derivative.

BACKGROUND ART

Various electron-accepting skeletons such as naphthobischalcogenadiazole are being researched in terms of their applications as an acceptor unit of an organic semiconductor polymeric material and as a basic skeleton of a low-molecular material. Thin films containing organic materials exhibiting such semiconductor characteristics are expected to be applied to photoelectric conversion elements such as an organic thin film solar cell and a light sensor, an organic electroluminescent element, and an organic thin film transistor. A naphthobischalcogenadiazole compound is reported to exhibit a good n-type organic field-effect transistor characteristic by reflecting its high electron-accepting capability (Patent Literature 1, Non-patent Literature 1). Moreover, a donor-acceptor type polymer constituted by introducing a naphthobischalcogenadiazole skeleton as an acceptor portion is reported to exhibit extremely high photoelectric conversion efficiency (Patent Literatures 2 and 3, Non-patent Literature 2). Furthermore, Patent Literature 4 discloses a polymer for organic semiconductor device constituted by repeating units in which a chlorine atom or an alkyl group is introduced at positions 5 and 10 of a naphthobisthiadiazol skeleton, and Patent Literature 5 discloses a p-type organic semiconductor material into which a fluorine atom has been introduced.

CITATION LIST

Patent Literature

Patent Literature 1: International Publication No. WO2014/178415
Patent Literature 2: International Publication No. WO2013/015298
Patent Literature 3: International Publication No. WO2015/029432
Patent Literature 4: U.S. Pat. No. 8,735,536
Patent Literature 5: Japanese Patent Application Publication Tokukai No. 2014-53383

Non-Patent Literature

Non-patent Literature 1: Macromolecules, 48, 576 (2015)
Non-patent Literature 2: J. Am. Chem. Soc. 135, 8834 (2013)

SUMMARY OF INVENTION

Technical Problem

In order to further improve the electron-accepting capability of the naphthobischalcogenadiazole skeleton for enhancing characteristics of the organic semiconductor material and expanding applications of the organic semiconductor material, modification of the naphthobischalcogenadiazole skeleton seems effective in which positions 5 and 10 of the naphthobischalcogenadiazole skeleton are modified with fluorine atoms which are substituent groups having strong electron-withdrawing property. However, Patent Literature 4 does not disclose a compound in which such modification is made. Although Patent Literature 5 discloses a compound in which the modification is made, Patent Literature 5 is silent about a feature of producing the compound via an intermediate having the same naphthobischalcogenadiazole skeleton. Therefore, under the current circumstances, it is difficult to systematically search and synthesize various naphthobischalcogenadiazole compounds having enhanced electron-accepting properties.

The present invention is accomplished in view of the circumstances, and an object of the present invention is to provide a naphthobischalcogenadiazole derivative and a method for producing the naphthobischalcogenadiazole derivative which can be used as a production intermediate having high versatility for producing a naphthobischalcogenadiazole compound into which a fluorine atom is introduced, which is a substituent group having a strong electron-withdrawing property for improving an electron-accepting property.

Solution to Problem

That is, a naphthobischalcogenadiazole derivative in accordance with an aspect of the present invention relates to a naphthobischalcogenadiazole derivative represented by a formula (I):

[Chem. 1]

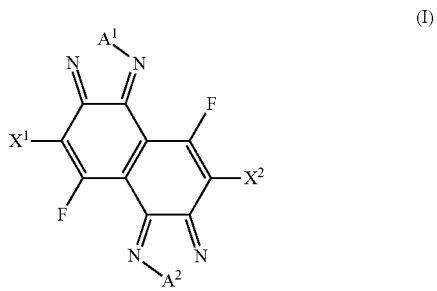

(I)

where each of $A^1$ and $A^2$ is independently an oxygen atom, a sulfur atom, a selenium atom, or a tellurium atom; and each of $X^1$ and $X^2$ is independently a hydrogen atom, a halogen atom, a boronic acid group, a boronic acid ester group, a boronic acid diaminonaphthalene amide group, an N-methyliminodiacetic acid boronate group, a trifluoroborate salt group, or a triolborate salt group.

Each of $A^1$ and $A^2$ in the formula (I) is preferably independently an oxygen atom, a sulfur atom, or a selenium atom. Both of $A^1$ and $A^2$ in the formula (I) are preferably sulfur atoms or selenium atoms. The naphthobischalcogenadiazole derivative in accordance with an aspect of the present invention is further preferably a naphthobisthiadiazol derivative in which both of $A^1$ and $A^2$ in the formula (I) are sulfur atoms.

Both of $X^1$ and $X^2$ in the formula (I) are preferably halogen atoms. Specific examples of halogen atoms represented by $X^1$ and $X^2$ in the formula (I) are preferably a fluorine atom, a chlorine atom, a bromine atom, or an iodine atom, more preferably a bromine atom or an iodine atom.

Both of $X^1$ and $X^2$ in the formula (I) are preferably boronic acid ester groups. Specific examples of the boronic acid ester groups represented by $X^1$ and $X^2$ in the formula (I) include boronic acid dialkyl ester groups such as a boronic acid dimethyl ester group, a boronic acid diethyl ester group, a boronic acid dipropyl ester group, a boronic acid diisopropyl ester group, a boronic acid dibutyl ester group, and a boronic acid dihexyl ester group; boronic acid dicycloalkyl ester groups such as a boronic acid dicyclohexyl ester group; boronic acid cyclic ester groups such as a boronic acid pinacol ester group, a boronic acid neopentyl glycol ester group, a boronic acid hexylene glycol ester group, a boronic acid catechol ester group, a boronic acid ethylene glycol ester group, a boronic acid propylene glycol ester group, a boronic acid 1,3-propanediol ester group, and a boronic acid 1,3-butandiol ester group; and the like, and the boronic acid ester group is preferably a boronic acid dialkyl ester group or a boronic acid cyclic ester group.

Specific examples of the naphthobischalcogenadiazole derivative represented by the formula (I) include compounds which are represented by structural formulae 1 through 60 below. In the structural formulae 1 through 60 below, R represents an alkyl group, and Me represents a methyl group.

[Chem. 2-1]

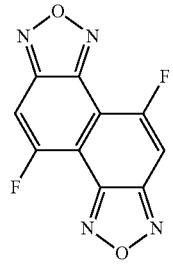

1

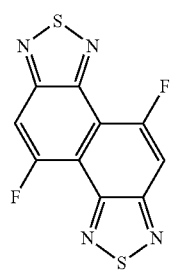

2

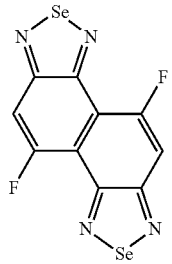

3

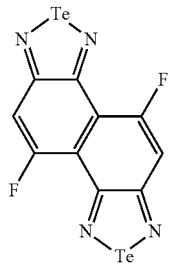

4

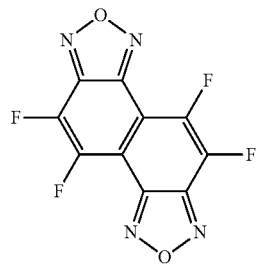

5

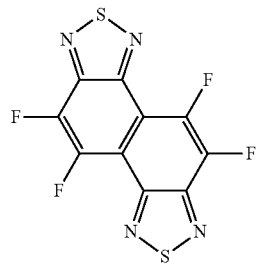

6

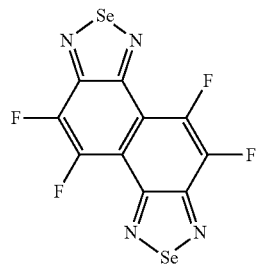

7

8

-continued
9
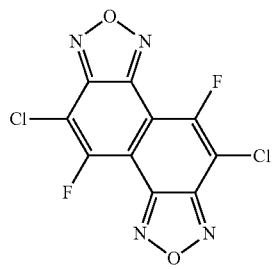
10
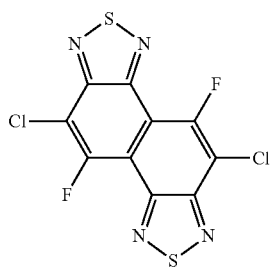
11
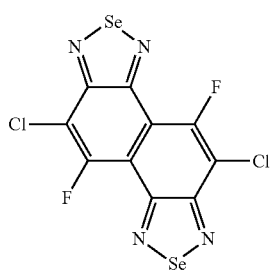
12
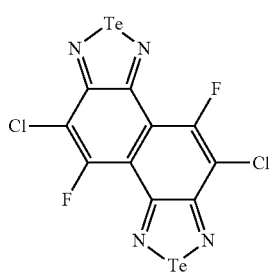
13
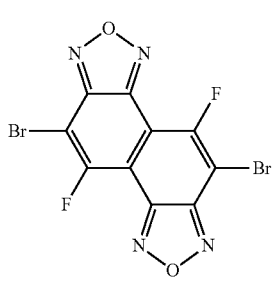
14
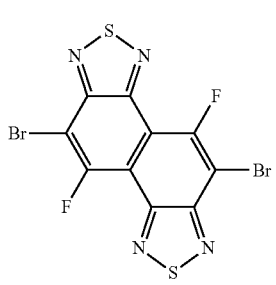
-continued
15
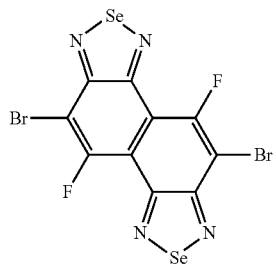
16
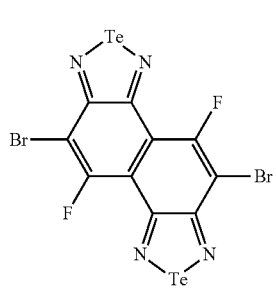
17
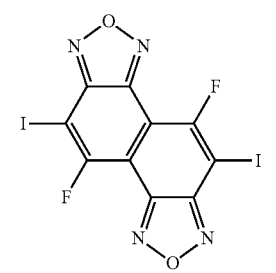
18
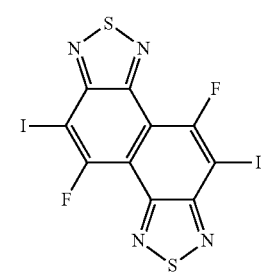
19
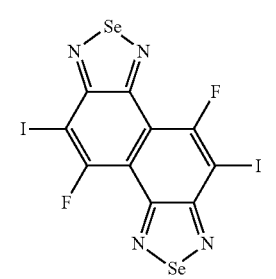
20
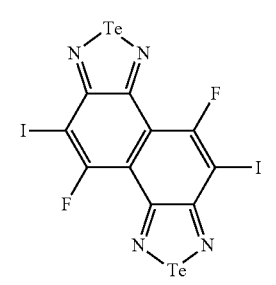

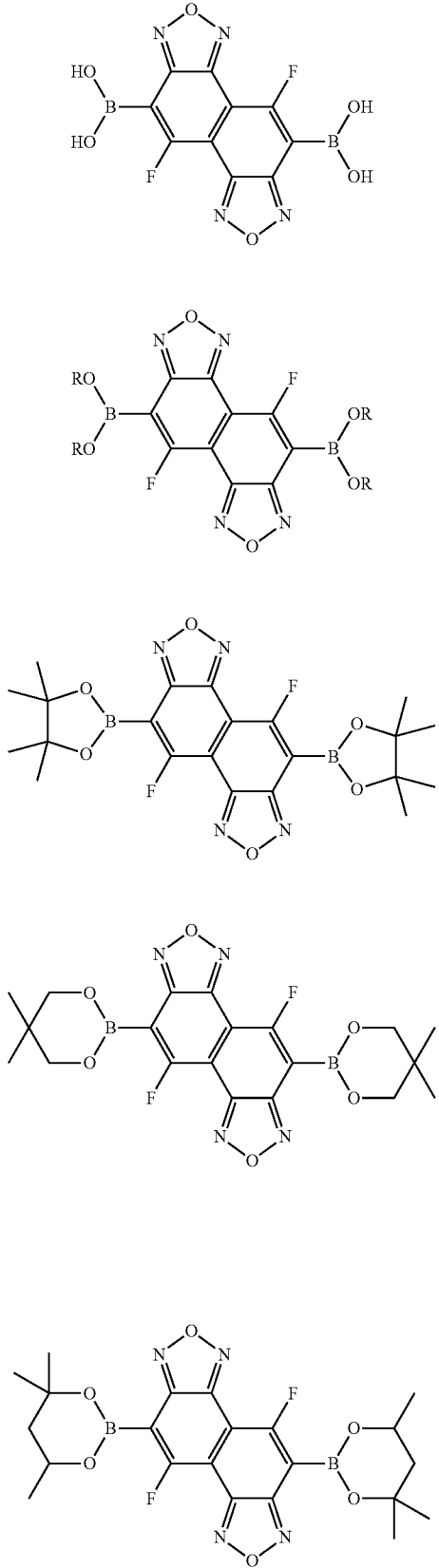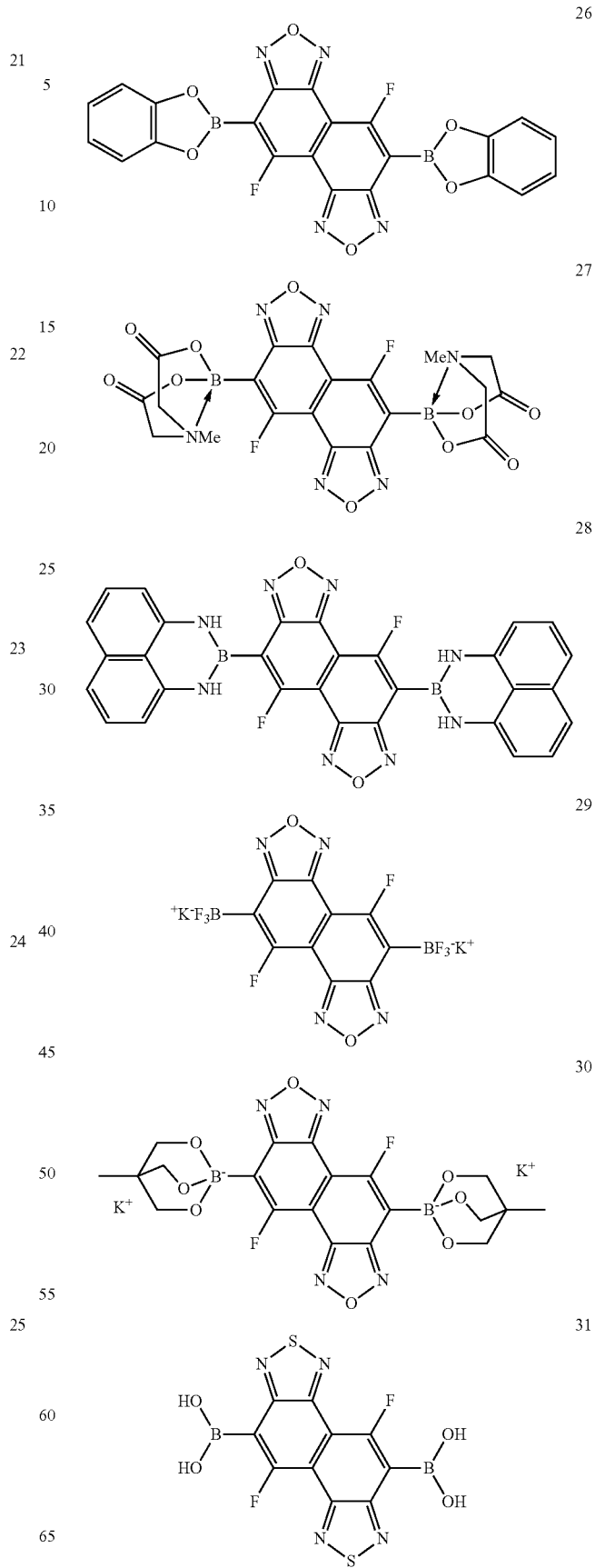

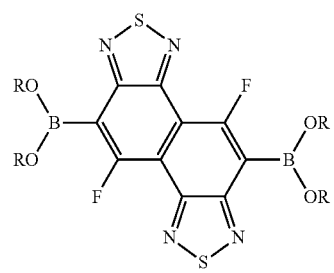
32
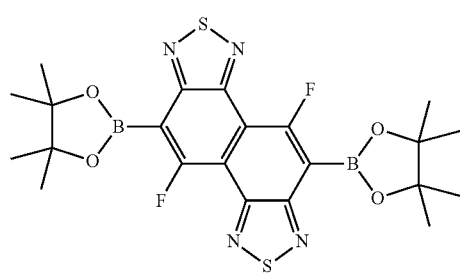
33
[Chem. 2-3]
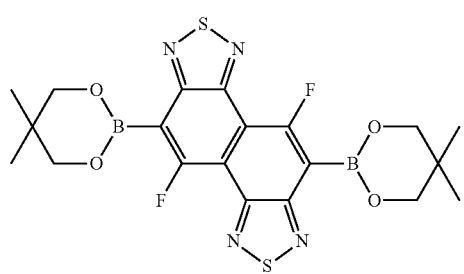
34
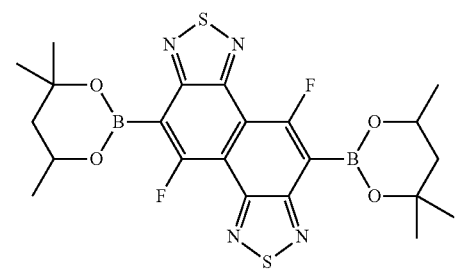
35
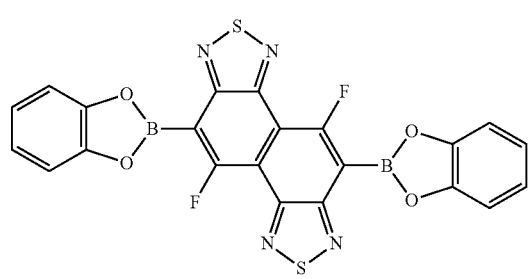
36
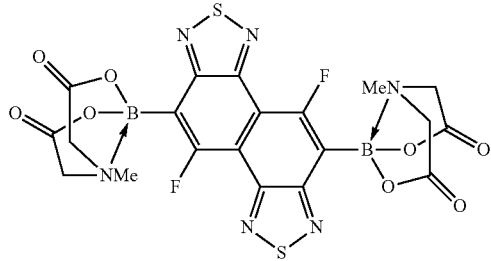
37
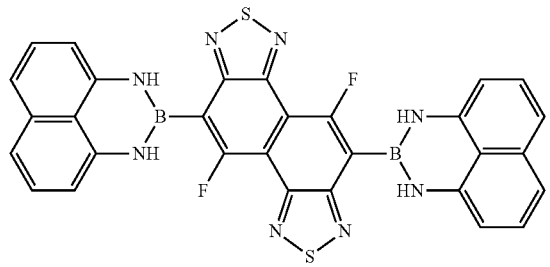
38
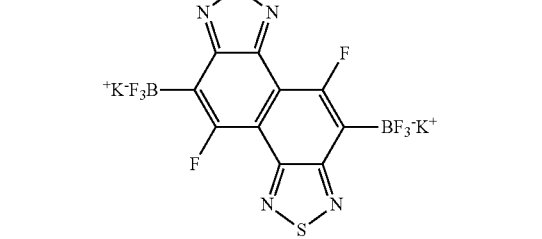
39
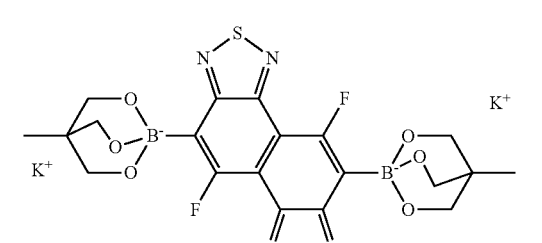
40
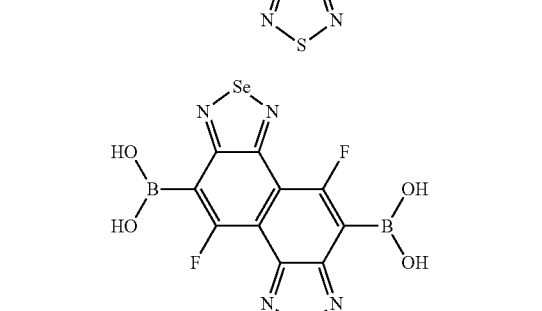
41
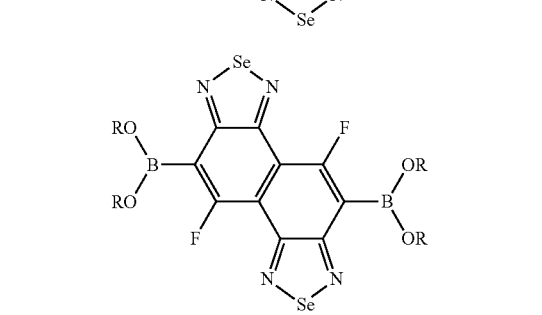
42

43
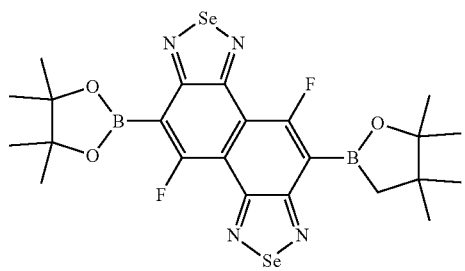
44
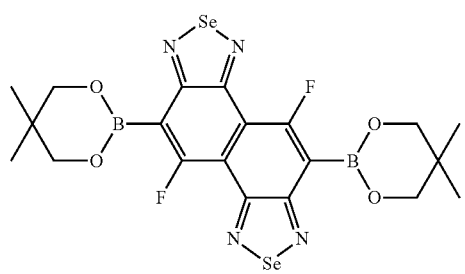
45
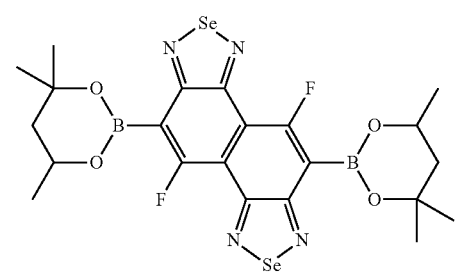
46
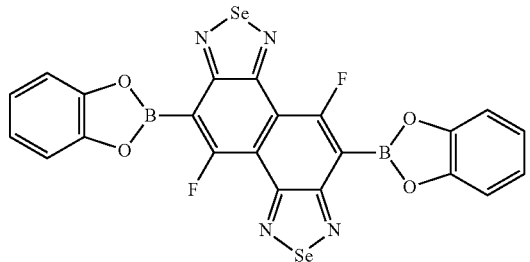
[Chem. 2-4]
47
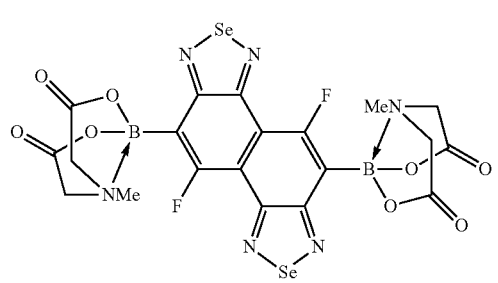
48
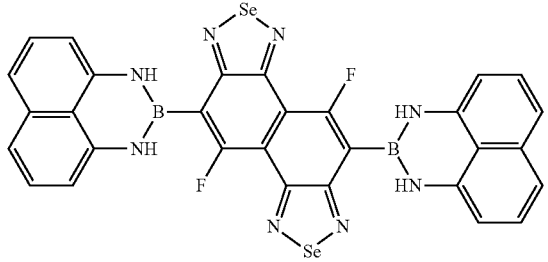
49
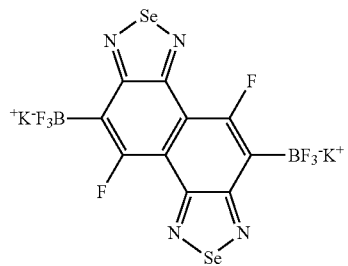
50
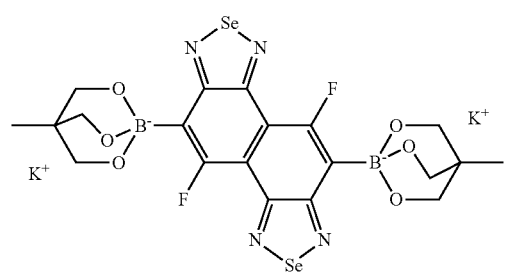
51
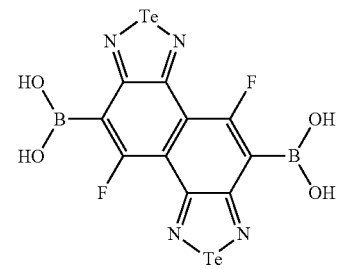
52
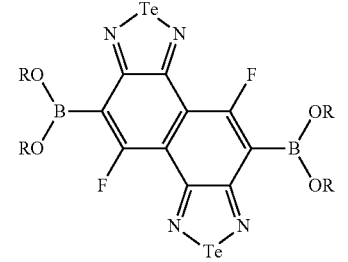
53
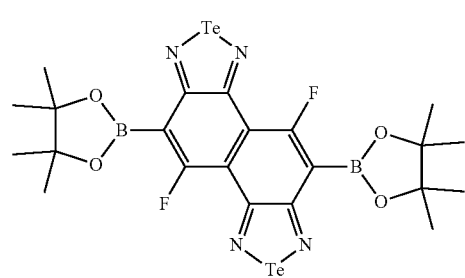

[Chem. 2-5]

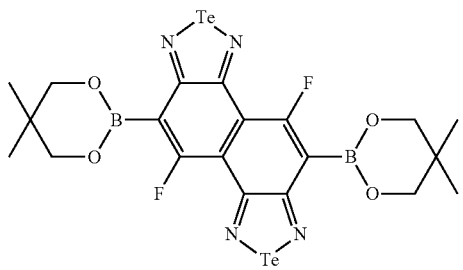
54

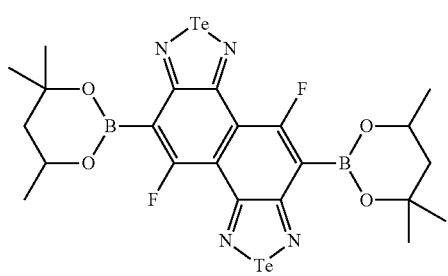
55

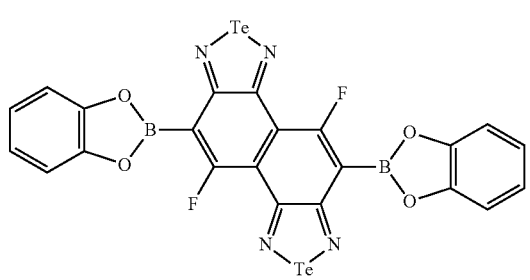
56

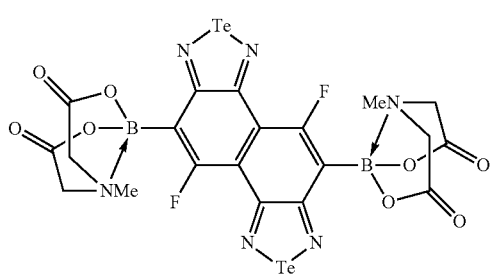
57

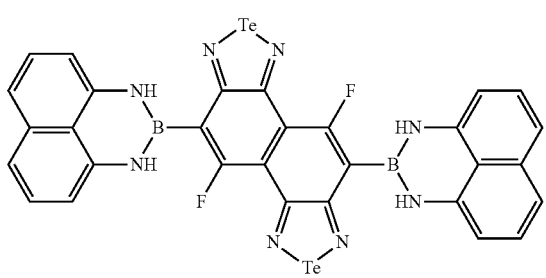
58

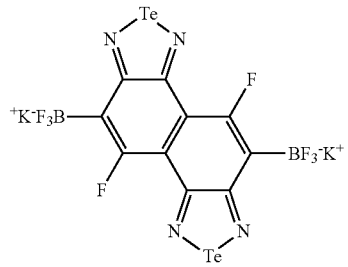
59

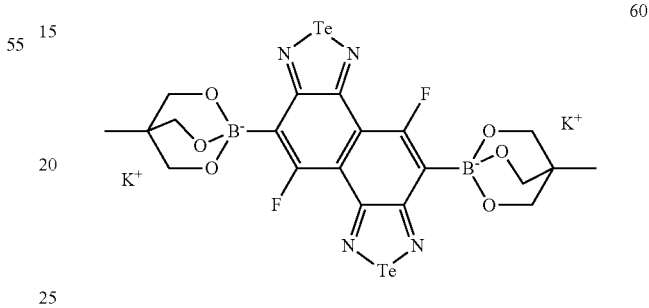
60

In this specification, unless otherwise noted, an alkyl group or an alkyl portion can be in a linear chain form or in a branched chain form. Specific examples of the alkyl group and the alkyl portion include $C_1$-$C_{10}$ alkyl such as methyl, ethyl, propyl, isopropyl, butyl, isobutyl, sec-butyl, tert-butyl, pentyl, hexyl, and decyl.

The production method in accordance with an aspect of the present invention is a method for producing the naphthobischalcogenadiazole derivative, and includes the step of causing tetraamino-difluoronaphthalene or hydrochloride thereof to react with a sulfurizing agent, a selenizing agent, or a tellurizing agent.

The production method in accordance with an aspect of the present invention is a method for producing the naphthobischalcogenadiazole derivative and includes the step of oxidizing and then reducing diamino-difluoro-dinitronaphthalene or hydrochloride thereof.

The production method in accordance with an aspect of the present invention is a method for producing the naphthobischalcogenadiazole derivative and includes the steps of causing tetraamino-difluoronaphthalene or hydrochloride thereof to react with a sulfurizing agent, a selenizing agent, or a tellurizing agent, and then causing a naphthobischalcogenadiazole derivative, which has been obtained in the above step, to react with a halogenating agent or a boronizing agent.

The production method in accordance with an aspect of the present invention is a method for producing the naphthobischalcogenadiazole derivative and includes the steps of oxidizing and then reducing diamino-difluoro-dinitronaphthalene or hydrochloride thereof, and causing a naphthobischalcogenadiazole derivative, which has been obtained in the above step, to react with a halogenating agent or a boronizing agent.

The production method in accordance with an aspect of the present invention preferably includes the step of producing tetraamino-difluoronaphthalene or hydrochloride thereof by reducing diamino-difluoro-dinitronaphthalene or hydrochloride thereof.

The production method in accordance with an aspect of the present invention preferably includes the step of producing diamino-difluoro-dinitronaphthalene or hydrochloride thereof by subjecting diamino-difluoronaphthalene or hydrochloride thereof to nitration reaction.

The production method in accordance with an aspect of the present invention preferably includes the step of producing diamino-difluoronaphthalene or hydrochloride thereof by subjecting difluoronaphthalene to amination reaction.

The production method in accordance with an aspect of the present invention preferably includes the step of producing difluoronaphthalene by subjecting diaminonaphthalene to fluorination reaction.

Advantageous Effects of Invention

The present invention can bring about an effect of providing the naphthobischalcogenadiazole derivative into which a fluorine atom has been introduced and which is useful as an intermediate of an organic semiconductor material that excels in electron-accepting property.

DESCRIPTION OF EMBODIMENTS

The following description will discuss details of suitable embodiments of the present invention.

The naphthobischalcogenadiazole derivative in accordance with an aspect of the present invention encompasses a compound having a halogen atom and a boron atom, and is applicable to organic metal catalytic reaction such as Suzuki coupling reaction, Stille coupling reaction, Negishi coupling reaction, Sonogashira coupling reaction, or oxidative coupling reaction. From this, the naphthobischalcogenadiazole derivative in accordance with an aspect of the present invention can be converted into various extended π electron system compounds through those reactions. For example, with reference to a method described in Angewandte Chemie International Edition, vol. 51, pages 5062 through 5085 (2012), it is possible to synthesize, from the naphthobischalcogenadiazole derivative in accordance with an aspect of the present invention, various naphthobischalcogenadiazole compounds into which a fluorine atom has been introduced.

Therefore, on the basis of the naphthobischalcogenadiazole derivative in accordance with an aspect of the present invention, it is possible to carry out research and to seek development and commercialization of a low-molecular compound and a polymeric material that have a naphthobischalcogenadiazole skeleton into which a fluorine atom has been introduced and are useful for various organic semiconductor materials.

The naphthobischalcogenadiazole derivative represented by the above formula (I) can be synthesized by combining production processes [A] through [U] described below as appropriate depending on a starting material (raw material).

Salts of compounds in the production processes [A] through [U] below encompass any kinds of salts that are acceptable in this technical field. Specific examples of the salts include salts with inorganic acids such as hydrochloric acid, hydrobromic acid, sulfuric acid, and phosphoric acid; salts with organic carboxylic acids such as tartaric acid, formic acid, acetic acid, citric acid, fumaric acid, maleic acid, trichloroacetic acid, and trifluoroacetic acid; salts with sulfonic acids such as methanesulfonic acid, benzenesulfonic acid, p-toluenesulfonic acid, mesitylenesulfonic acid, and naphthalenesulfonic acid; and the like.

Production Process [A]

The production process [A] is a process for producing a naphthobisoxadiazole derivative represented by a formula (I-I) or a formula (I-II) from a compound represented by a formula (II), a formula (III), or a formula (IV) below. The production process [A] includes a first step, a second step, and a third step below.

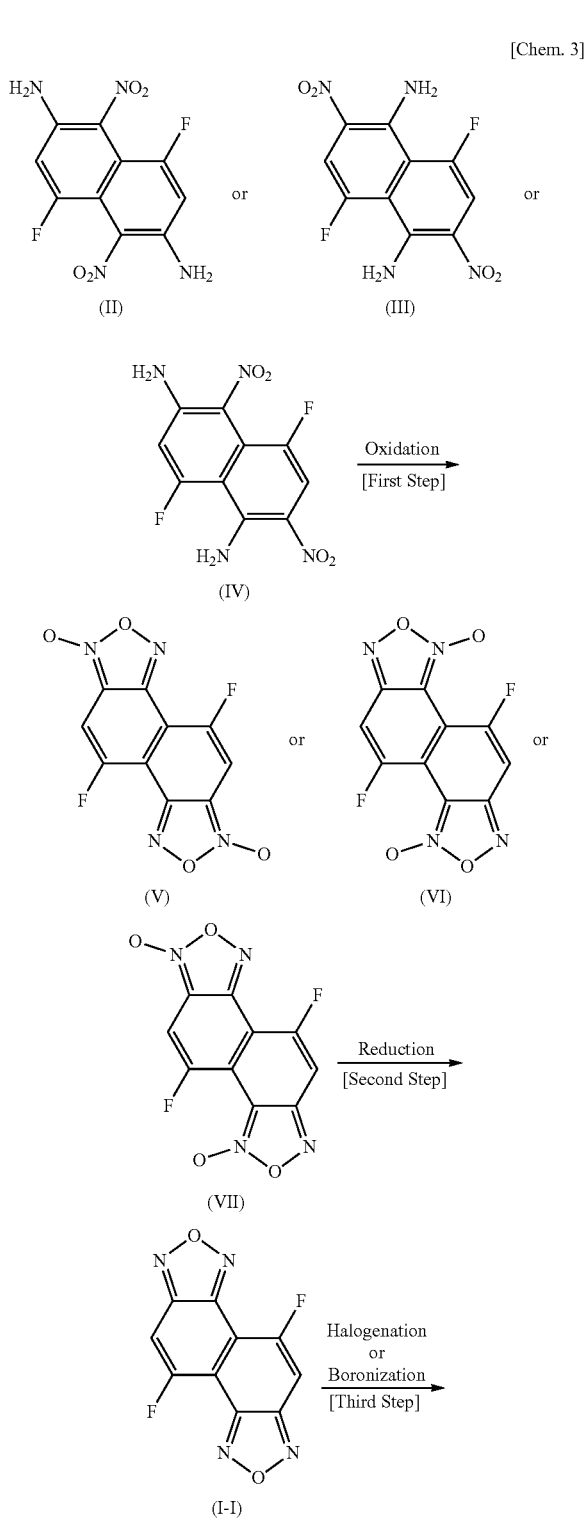

[Chem. 3]

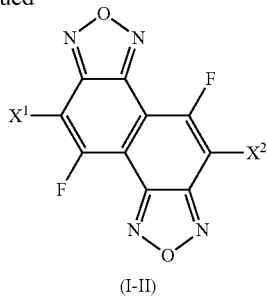

(I-II)

In the first step of the production process [A], the compound represented by the formula (II), the formula (III), or the formula (IV) is caused to react (oxidation reaction) with an oxidizer so as to produce a compound represented by a formula (V), a formula (VI), or a formula (VII). Note that the compounds represented by the respective formulae (II) through (IV) can be salts.

The oxidizer is not limited to a particular one, provided that the reaction proceeds with use of the oxidizer. Examples of the oxidizer include oxygen gas, ozone gas, chromic oxide, potassium permanganate, hydrogen peroxide, m-chloroperbenzoic acid, ruthenium tetroxide, and the like. The oxidizer can be used in an equivalent weight of 1 to 20, preferably in an equivalent weight of 1 to 5, with respect to 1 equivalent weight of the compound represented by the formula (II), the formula (III), or the formula (IV).

The reaction in the first step of the production process [A] can be typically carried out in the presence of a base and a solvent and, optionally, in the presence of a phase transfer catalyst.

The base is not limited to a particular one, provided that the reaction proceeds with use of the base. Examples of the base include alkali metal carbonate such as sodium carbonate, potassium carbonate, and cesium carbonate; alkali metal alkoxide such as sodium methoxide, sodium ethoxide, and potassium tertiary butoxide; hydrogencarbonate of alkali metal such as sodium hydrogencarbonate; carbonate of alkaline-earth metal such as calcium carbonate; metal hydroxide such as sodium hydroxide and potassium hydroxide; metal hydride such as sodium hydride and potassium hydride; organic amines such as triethylamine, diisopropylethylamine, pyridine, and 4-(N,N-dimethylamino)pyridine; and the like. The base can be used in an equivalent weight of 1 to 20, preferably in an equivalent weight of 1 to 5, with respect to 1 equivalent weight of the compound represented by the formula (II), the formula (III), or the formula (IV).

The solvent is not limited to a particular one, provided that the reaction proceeds with use of the solvent. Examples of the solvent include aromatic hydrocarbons such as benzene, toluene, xylene, and chlorobenzene; alcohols such as methyl alcohol, ethyl alcohol, and isopropyl alcohol; aliphatic hydrocarbons such as hexane, heptane, petroleum ether, ligroin, and cyclohexane; halogenated hydrocarbons such as chloroform, dichloromethane, carbon tetrachloride, and 1,2-dichloroethane; ethers such as diethyl ether, diisopropyl ether, dibutyl ether, tetrahydrofuran, dioxane, and ethylene glycol dimethyl ether; esters such as methyl acetate and ethyl acetate; polar aprotic solvents such as dimethyl sulfoxide, sulfolane, dimethylacetamide, dimethylformamide, N-methylpyrrolidone, and pyridine; nitriles such as acetonitrile, propionitrile, and acrylonitrile; ketones such as acetone and methyl ethyl ketone; water; inorganic acids such as hydrochloric acid and sulfuric acid; organic acids such as acetic acid, trifluoroacetic acid, and methanesulfonic acid; mixed solvents of these solvents; and the like. It is possible to select one of or two or more (mixed solvent) of these as appropriate. Moreover, in addition to these solvents, it is possible to use, as a solvent(s), any of organic amines from among the above exemplified bases.

Examples of the phase transfer catalyst include quaternary ammonium salts such as tetrabutylammonium chloride, tetrabutylammonium bromide, and tetrabutylammonium iodide; crown ether such as 18-crown-6; phosphonium salts such as alkyltributylphosphonium bromide; and the like.

A reaction temperature in the first step is typically 0° C. to 200° C., preferably 0° C. to 120° C. A reaction time is typically 1 hour to 48 hours.

In the second step of the production process [A], the compound represented by the formula (V), the formula (VI), or the formula (VII) is caused to react (reduction reaction) with a reducing agent so as to produce a compound represented by a formula (I-I). Note that, in a case where the compound of the formula (I-I) is directly obtained from the compound represented by the formula (II), the formula (III), or the formula (IV) by the oxidation in the first step, it is possible to omit the second step.

The reducing agent is not limited to a particular one, provided that the reaction proceeds with use of the reducing agent. Examples of the reducing agent include hydroxylamine hydrochloride, trimethyl phosphate, triethyl phosphite, triphenylphosphine, sulfur, ethylene glycol, and the like. The reducing agent can be used in an equivalent weight of 1 to 20, preferably in an equivalent weight of 1 to 5, with respect to 1 equivalent weight of the compound represented by the formula (V), the formula (VI), or the formula (VII).

The second step of the production process [A] can be carried out, typically, in the presence of a base and a solvent. The base is not limited to a particular one, provided that the reaction proceeds with use of the base. Examples of the base include the bases for use in the first step. The base can be used in an equivalent weight of 1 to 20, preferably in an equivalent weight of 1 to 5, with respect to 1 equivalent weight of the compound represented by the formula (II), the formula (III), or the formula (IV).

The solvent is not limited to a particular one, provided that the reaction proceeds with use of the solvent. Examples of the solvent include the solvents for use in the first step.

A reaction temperature in the second step is typically 0° C. to 200° C., preferably 0° C. to 120° C. A reaction time is typically 1 hour to 48 hours.

In the third step of the production process [A], the compound of the formula (I-I) is caused to react (halogenation reaction or boronization reaction) with a halogenating agent or a boronizing agent so as to produce a compound represented by the formula (I-II).

The halogenating agent is not limited to a particular one, provided that the reaction proceeds with use of the halogenating agent. Examples of the halogenating agent include N-chlorosuccinimide, bromine, N-bromosuccinimide, N-iodosuccinimide, and the like. The halogenating agent can be used in an equivalent weight of 1 to 20, preferably in an equivalent weight of 1 to 5, with respect to 1 equivalent weight of the compound of the formula (I-I).

The boronizing agent is not limited to a particular one, provided that the reaction proceeds with use of the boronizing agent. Examples of the boronizing agent include bis(pinacolato)diboron, bis(neopentyl glycolato)diboron, bis(hexylene glycolato)diboron, bis(catecholato)diboron, and the like. The boronizing agent can be used in an equivalent weight of 1 to 20, preferably in an equivalent weight of 1 to 5, with respect to 1 equivalent weight of the compound of the formula (I-I).

In the boronization, it is possible to carry out the reaction optionally in the presence of an organic metal catalyst, an organic ligand, and a base.

Examples of the organic metal catalyst include palladium catalysts such as bis(triphenylphosphine)palladiumdichloride, tetrakis(triphenylphosphine)palladium, [1,1'-bis(diphenylphosphino)ferrocene]palladium(II)dichloride, and bis(tri-tert-butylphosphine)palladium; iridium catalysts such as bis(1,5-cyclooctadiene)di-μ-methoxydiiridium; and the like. The organic metal catalyst can be used in an equivalent weight of 0.001 to 5, preferably in an equivalent weight of 0.01 to 1, with respect to 1 equivalent weight of the compound of the formula (I-I).

Examples of the organic ligand include 4,4'-di-tert-butyl-2,2'-dipyridyl, and the like. The organic ligand can be used in an equivalent weight of 0.001 to 5, preferably in an equivalent weight of 0.01 to 1, with respect to 1 equivalent weight of the compound of the formula (I-I).

The base is not limited to a particular one, provided that the reaction proceeds with use of the base. Examples of the base include the bases for use in the first step or in the second step. The base can be used in an equivalent weight of 1 to 20, preferably in an equivalent weight of 1 to 5, with respect to 1 equivalent weight of the compound of the formula (I-I).

The solvent is not limited to a particular one, provided that the reaction proceeds with use of the solvent. Examples of the solvent include the solvents for use in the first step.

A reaction temperature in the third step is typically 0° C. to 200° C., preferably 0° C. to 120° C. A reaction time is typically 1 hour to 48 hours.

Production Process [B]

The production process [B] is a process for producing a naphthobischalcogenadiazole derivative represented by a formula (I-III) or a formula (I-IV) from a compound represented by a formula (VIII). The production process [B] includes a first step and a second step below.

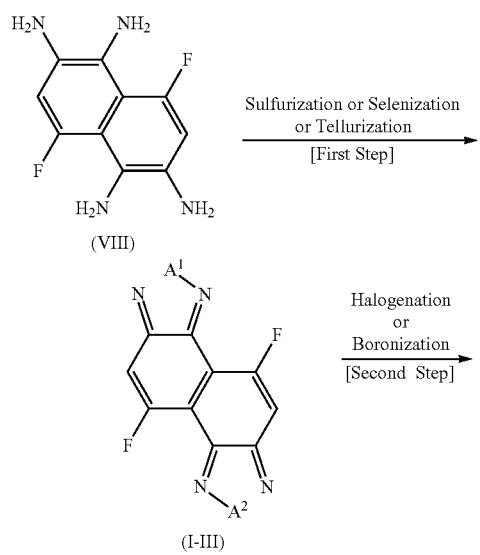

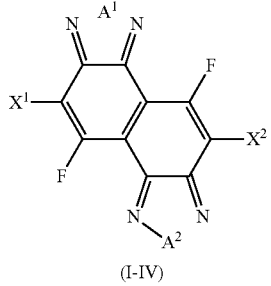

In the first step of the production process [B], the compound of the formula (VIII) is reacted (sulfurization reaction, selenization reaction, or tellurization reaction) with a sulfurizing agent, a selenizing agent, or a tellurizing agent so as to produce a compound represented by the formula (I-III).

The sulfurizing agent is not limited to a particular one, provided that the reaction proceeds with use of the sulfurizing agent. Examples of the sulfurizing agent include sulfur, sulfur monochloride, sulfur dichloride, thionyl chloride, sulfuryl chloride, 2,4-bis(4-methoxyphenyl)-1,3,2,4-dithiadiphosphetane-2,4-disulfide, and the like. The sulfurizing agent can be used in an equivalent weight of 1 to 20, preferably in an equivalent weight of 1 to 5, with respect to 1 equivalent weight of the compound of the formula (VIII).

The selenizing agent is not limited to a particular one, provided that the reaction proceeds with use of the selenizing agent. Examples of the selenizing agent include selenium tetrachloride, selenium hexachloride, selenium tetrabromide, selenium tetraiodide, selenious acid, selenium dioxide, selenium oxychloride, and the like. The selenizing agent can be used in an equivalent weight of 1 to 20, preferably in an equivalent weight of 1 to 5, with respect to 1 equivalent weight of the compound of the formula (VIII).

The tellurizing agent is not limited to a particular one, provided that the reaction proceeds with use of the tellurizing agent. Examples of the tellurizing agent include tellurium tetrachloride, tellurium tetrabromide, tellurium tetraiodide, tellurium monoxide, tellurium dioxide, tellurium trioxide, tellurous acid, and the like. The tellurizing agent can be used in an equivalent weight of 1 to 20, preferably in an equivalent weight of 1 to 5, with respect to 1 equivalent weight of the compound of the formula (VIII).

The reaction in the first step of the production process [B] can be carried out, typically, in the presence of a base and a solvent.

The base is not limited to a particular one, provided that the reaction proceeds with use of the base. Examples of the base include the bases for use in the production process [A]. The base can be used in an equivalent weight of 1 to 20, preferably in an equivalent weight of 1 to 5, with respect to 1 equivalent weight of the compound of the formula (VIII).

The solvent is not limited to a particular one, provided that the reaction proceeds with use of the solvent. Examples of the solvent include the solvents for use in the first step of the production process [A].

A reaction temperature in the first step is typically 0° C. to 200° C., preferably 0° C. to 120° C. A reaction time is typically 1 hour to 48 hours.

In the second step of the production process [B], the compound of the formula (I-III) is caused to react (halogenation reaction or boronization reaction) with a halogenating agent or a boronizing agent so as to produce a compound represented by the formula (I-IV).

The halogenating agent or the boronizing agent is not limited to a particular one, provided that the reaction proceeds with use of the halogenating agent or the boronizing agent. Examples of the halogenating agent or the boronizing agent include the halogenating agents or the boronizing agents for use in the third step of the production process [A]. The halogenating agent can be used in an equivalent weight of 1 to 20, preferably in an equivalent weight of 1 to 5, with respect to 1 equivalent weight of the compound of the formula (I-III).

The boronization can be carried out optionally in the presence of an organic metal catalyst, an organic ligand, and a base.

The organic metal catalyst and the organic ligand are not limited to particular ones, provided that the reaction proceeds with use of the organic metal catalyst and the organic ligand. Examples of the organic metal catalyst and the organic ligand include the organic metal catalysts and the organic ligands for use in the third step of the production process [A]. The organic metal catalyst can be used in an equivalent weight of 0.001 to 5, preferably in an equivalent weight of 0.01 to 1, with respect to 1 equivalent weight of the compound of the formula (I-III). The organic ligand can be used in an equivalent weight of 0.001 to 5, preferably in an equivalent weight of 0.01 to 1, with respect to 1 equivalent weight of the compound of the formula (I-III).

The base is not limited to a particular one, provided that the reaction proceeds with use of the base. Examples of the base include the bases for use in the first step of the production process [A]. The base can be used in an equivalent weight of 1 to 20, preferably in an equivalent weight of 1 to 5, with respect to 1 equivalent weight of the compound of the formula (I-III).

The solvent is not limited to a particular one, provided that the reaction proceeds with use of the solvent. Examples of the solvent include the solvents for use in the second step of the production process [A].

A reaction temperature in the second step is typically 0° C. to 200° C., preferably 0° C. to 120° C. A reaction time is typically 1 hour to 48 hours.

Production Process [C]

The production process [C] is a process for producing the compound represented by the formula (II), the formula (III), the formula (IV), or the formula (VIII) from a compound represented by a formula (IX). The production process [C] includes the steps below.

In the formula (IX), U, V, W, X, Y, and Z are respectively six substituent groups binding to a naphthalene ring at positions other than positions at which hydrogen atoms are originally binding to the naphthalene ring. Each of the substituent groups is independently a hydrogen atom, a halogen atom (fluorine atom, chlorine atom, bromine atom, iodine atom, or the like), an amino group, a nitro group, a hydroxy group, a trifluoromethanesulfonyl group (OTf), a $B(OR^a)(OR^b)$ group, a boronic acid diaminonaphthalene amide group, an N-methyliminodiacetic acid boronate group, a trifluoroborate salt group, or a triolborate salt group. Each of $R^a$ and $R^b$ is independently a hydrogen atom or a $C_1$-$C_{10}$ alkyl group, and $(OR^a)$ and $(OR^b)$ can form a ring together. Substitution positions of the U, V, W, X, Y, and Z in the naphthalene ring are not particularly determined.

That is, the process of producing the compound of the formula (II), the formula (III), the formula (IV), or the formula (VIII) from the compound of the formula (IX) includes but not limited to at least one of nitration, halogenation, halogen substitution, boronization, hydroxylation, amination, protection, and deprotection, and is constituted by selecting and combining necessary processes from among these processes as appropriate depending on a structure of a starting material, i.e., a structure of the compound of the formula (IX). The selection and combination of the necessary processes (i.e., an order in which the selected processes are carried out) can be easily understood by a person skilled in the art based on the structure of the compound of the formula (IX) which is the starting material and on the structure of the compound of the formula (II), the formula (III), the formula (IV), or the formula (VIII) which is a substance to be obtained.

Examples of the compound of the formula (IX) include compounds represented by structural formulae below which are commercially available compounds and salts of these compounds.

[Chem. 6-1]

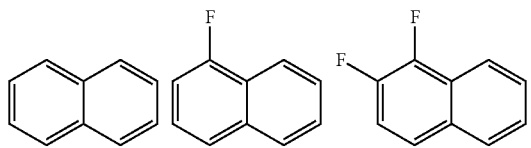

[Chem. 5]

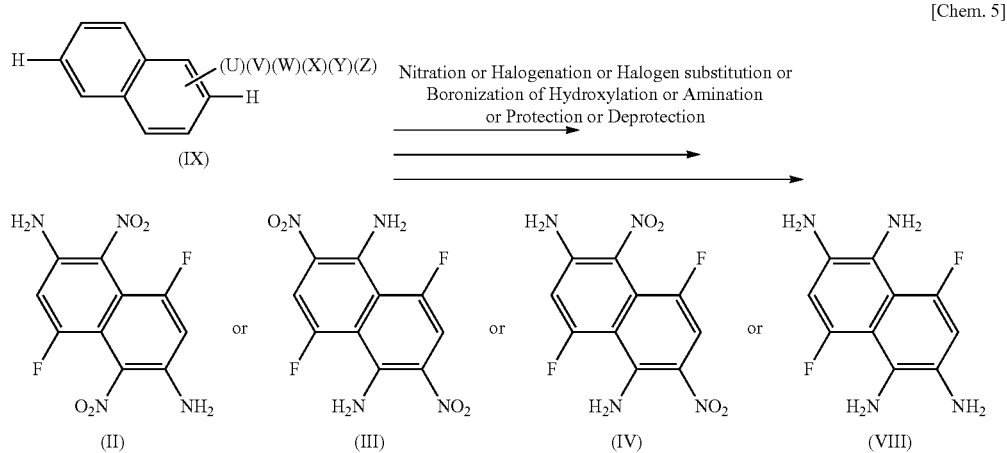

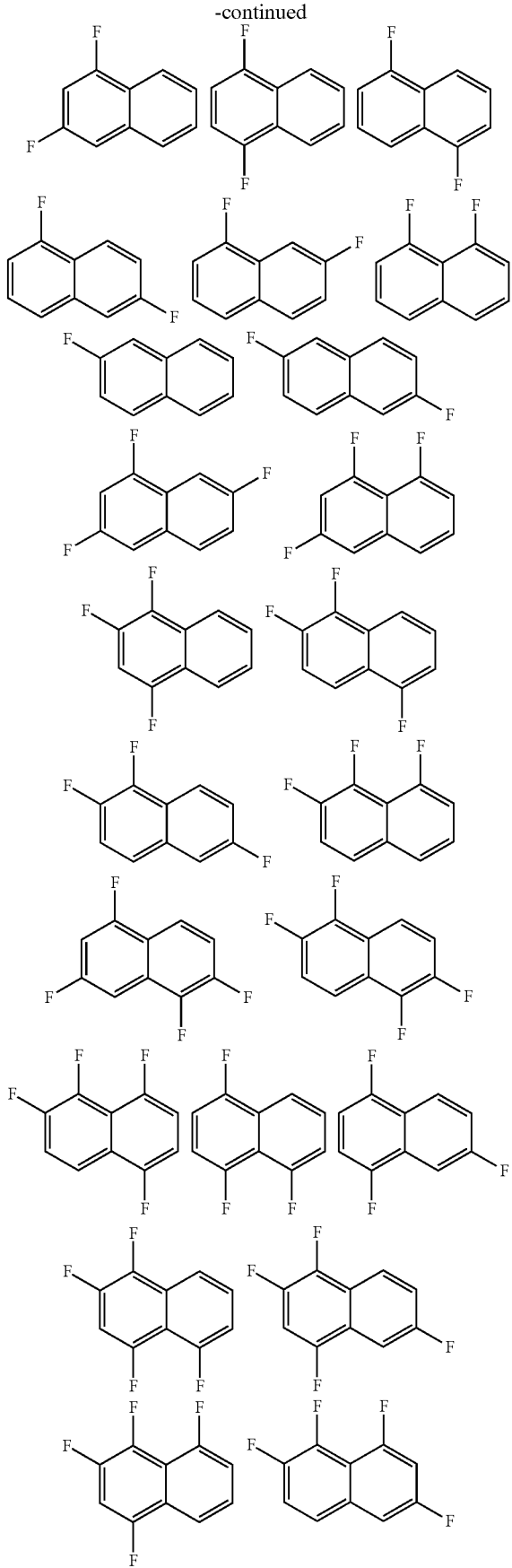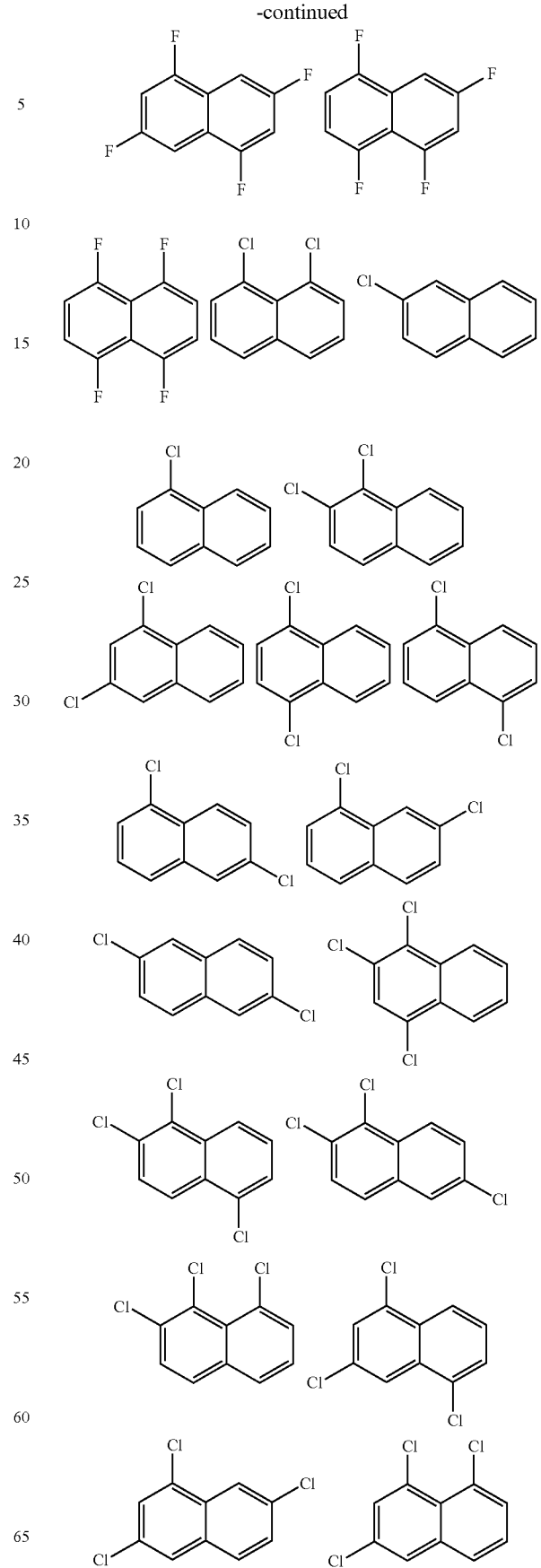

-continued
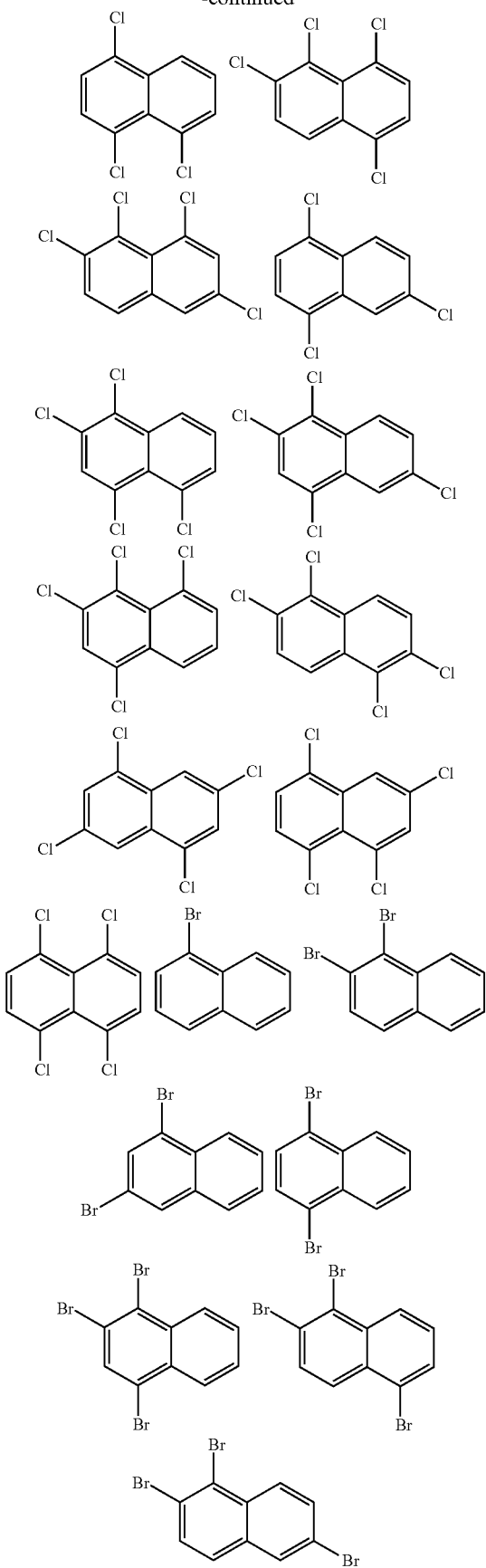
-continued
[Chem. 6-2]
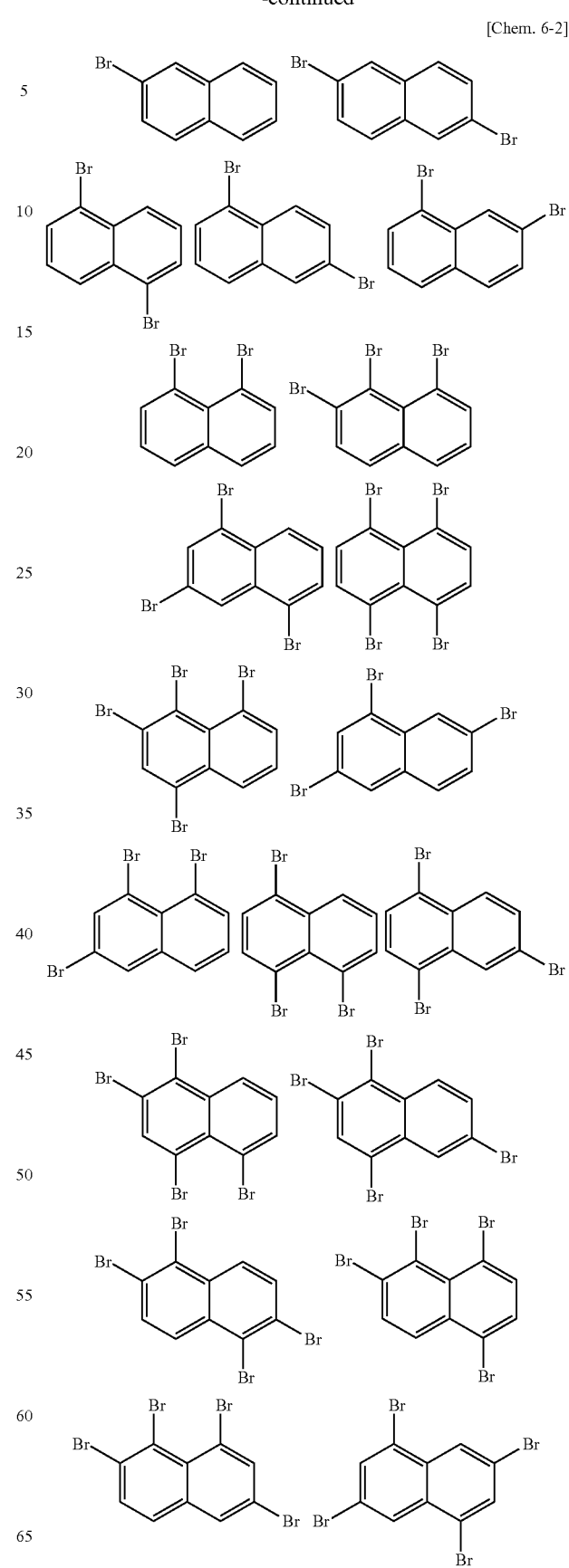

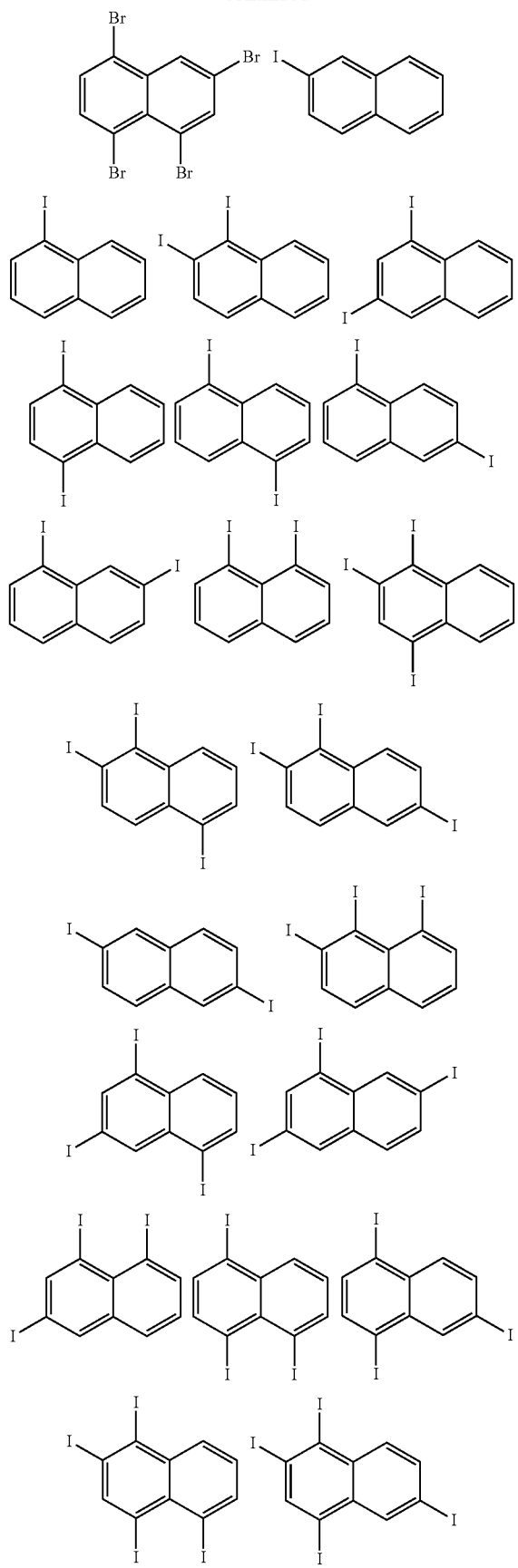
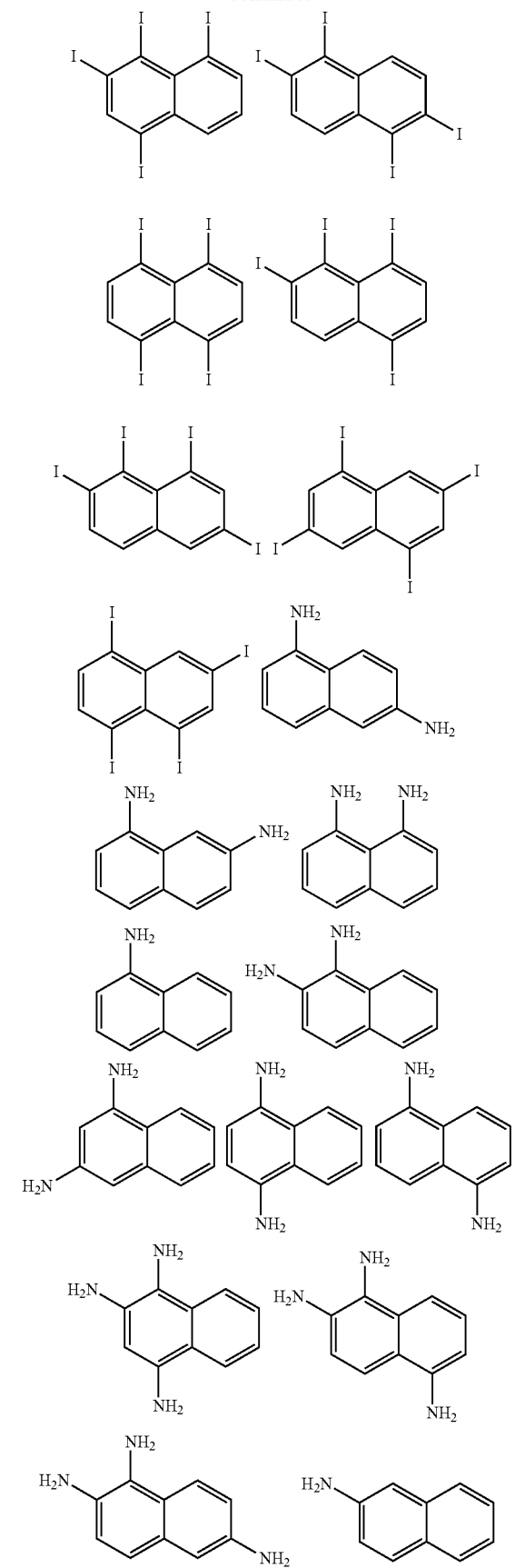

-continued
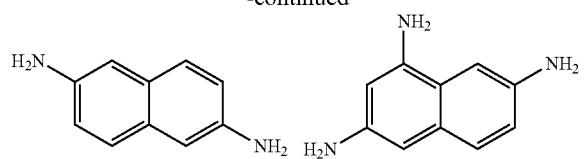
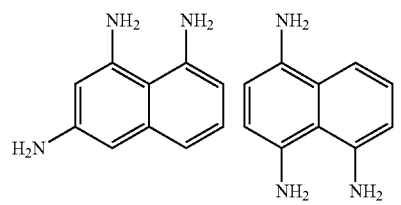
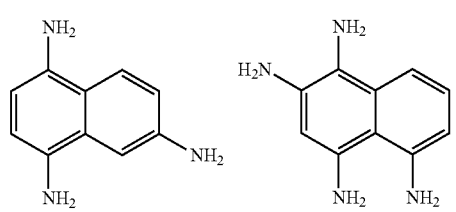
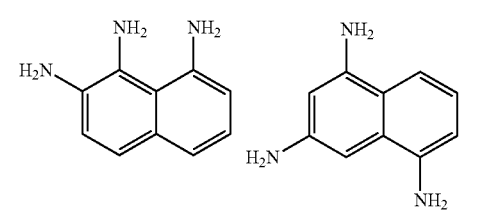
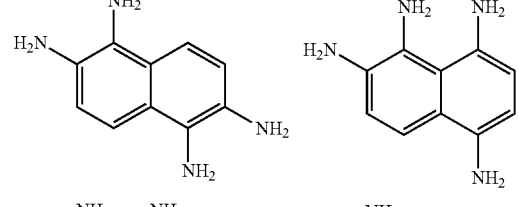
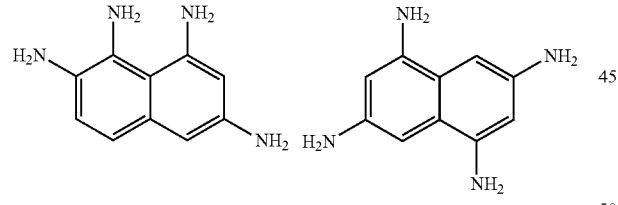
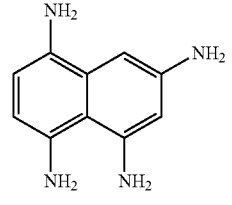
[Chem. 6-3]
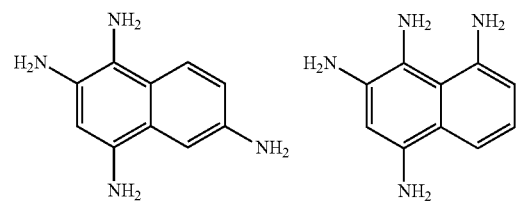
-continued
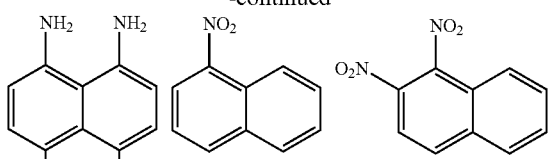
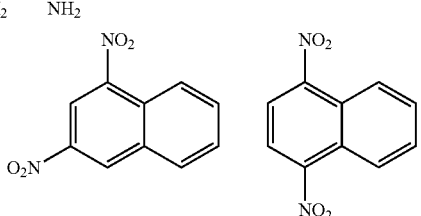
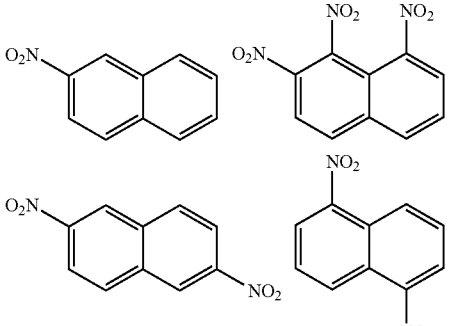
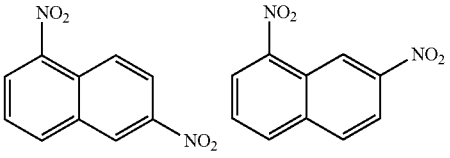
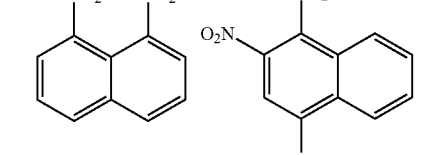
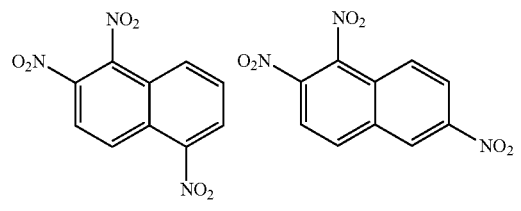
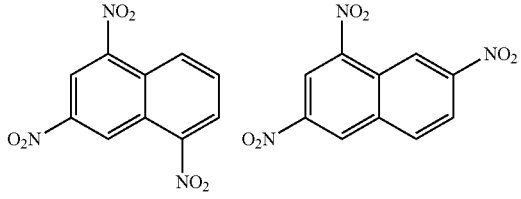
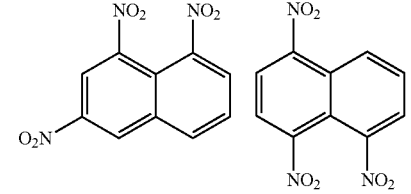

31
-continued
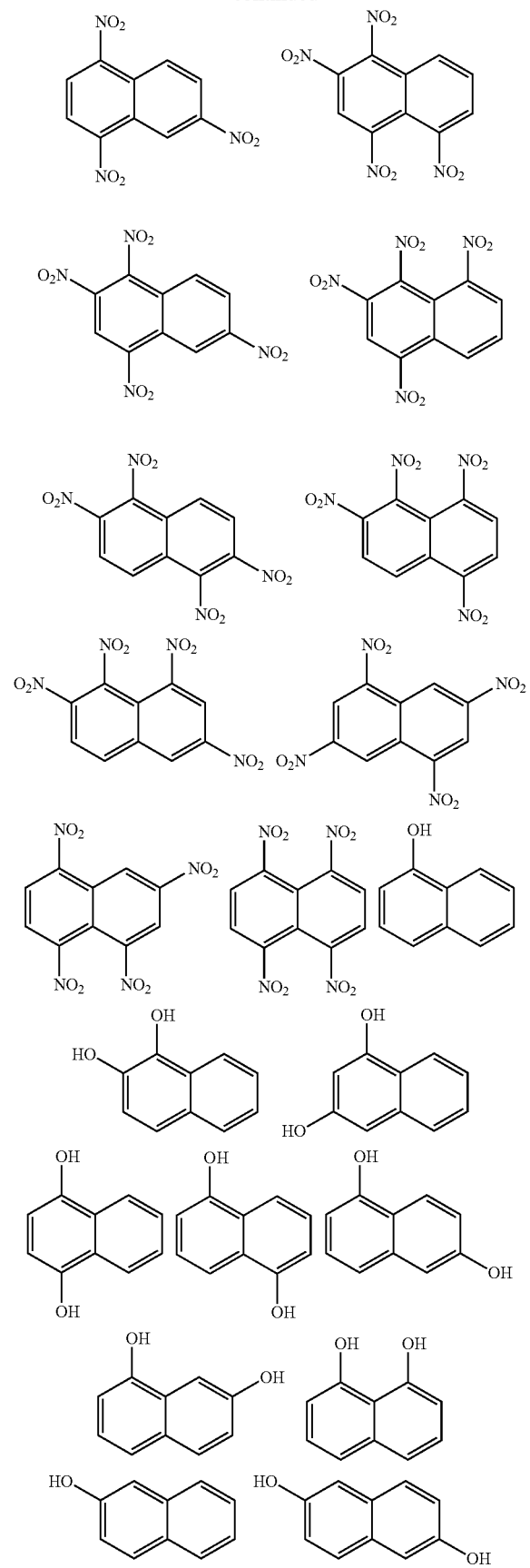
32
-continued
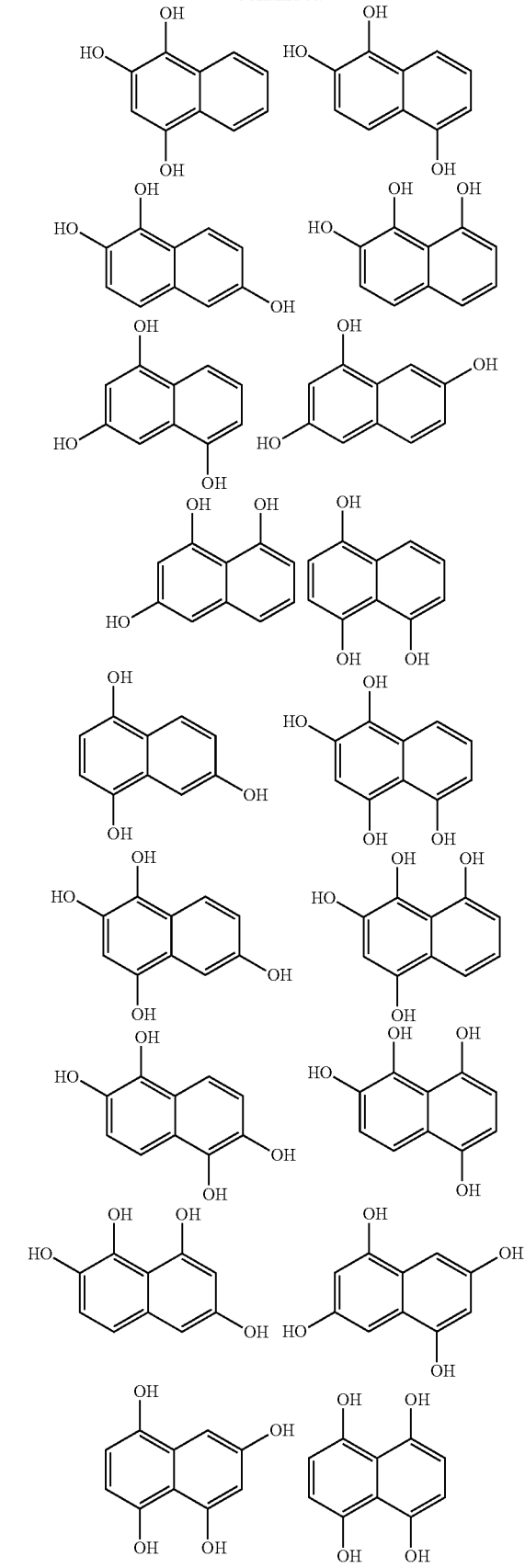

[Chem. 6-4]
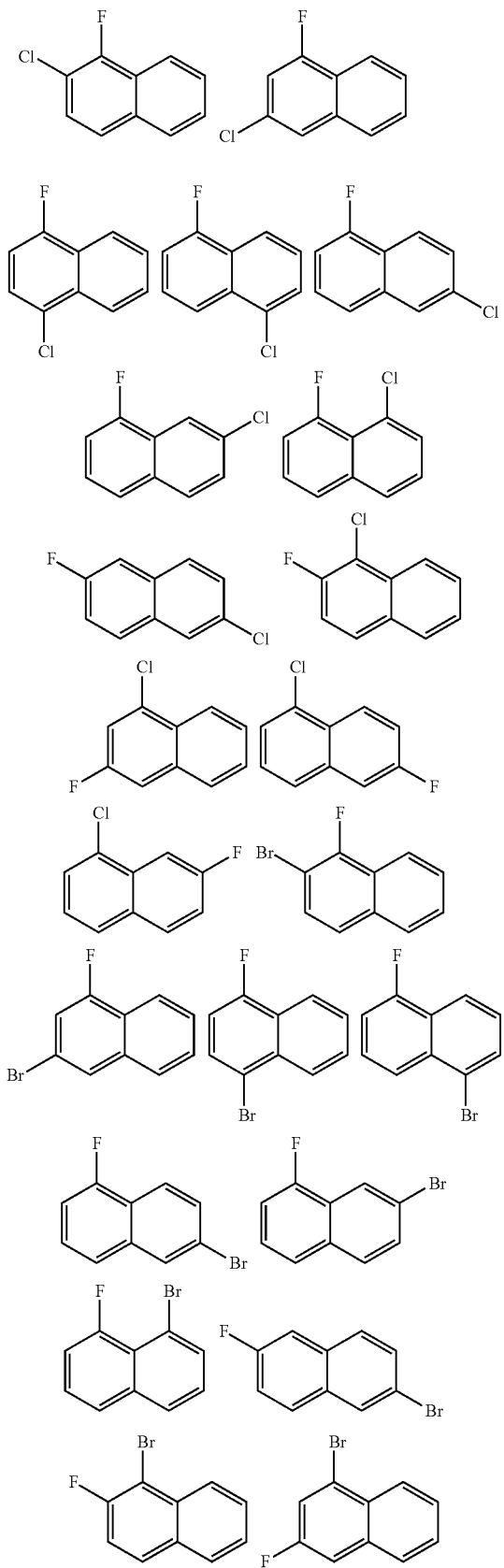
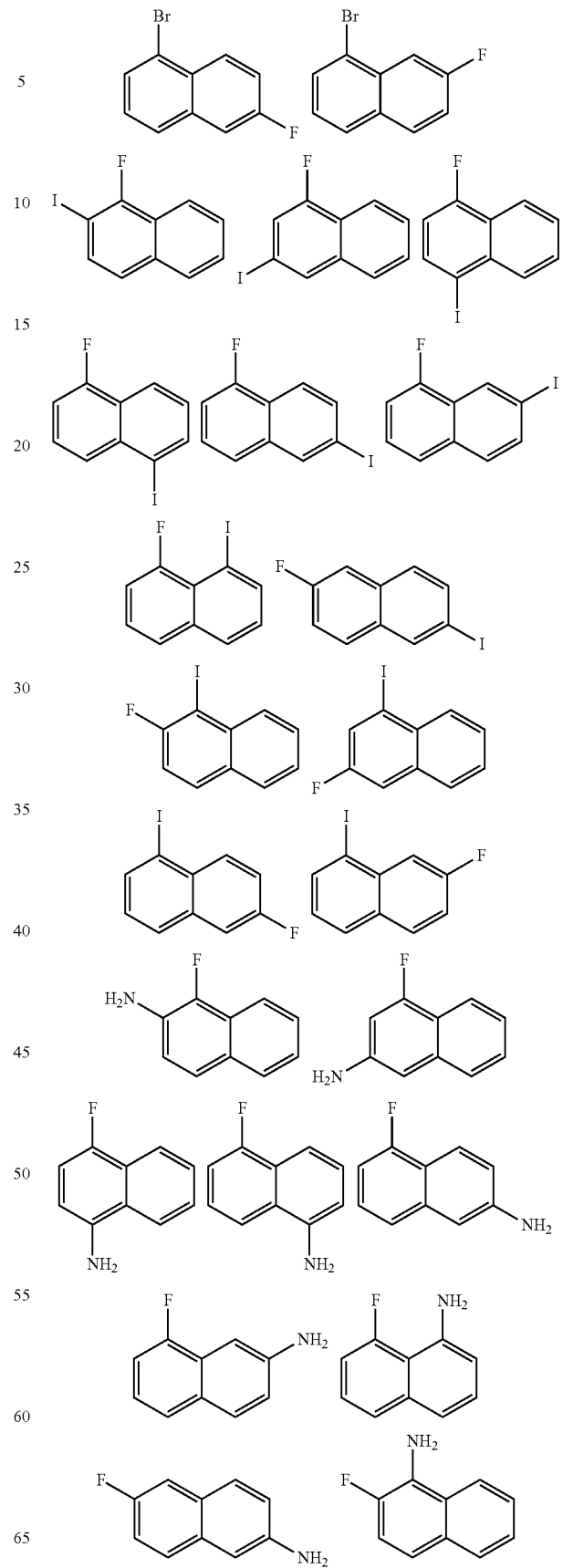

35
-continued
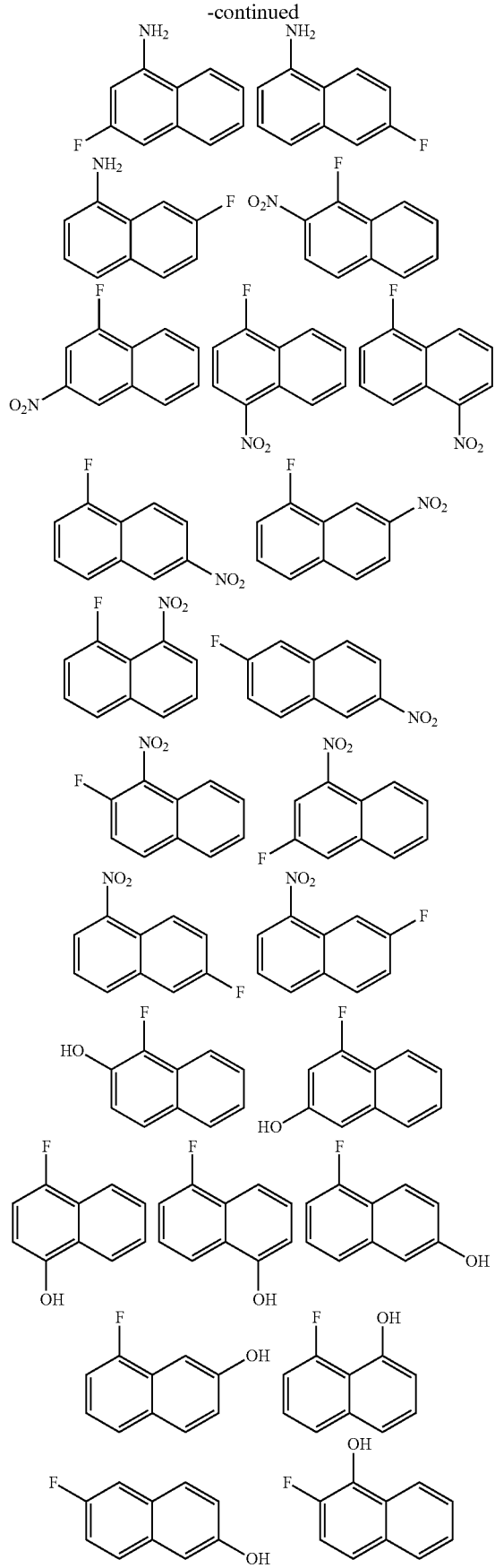
36
-continued
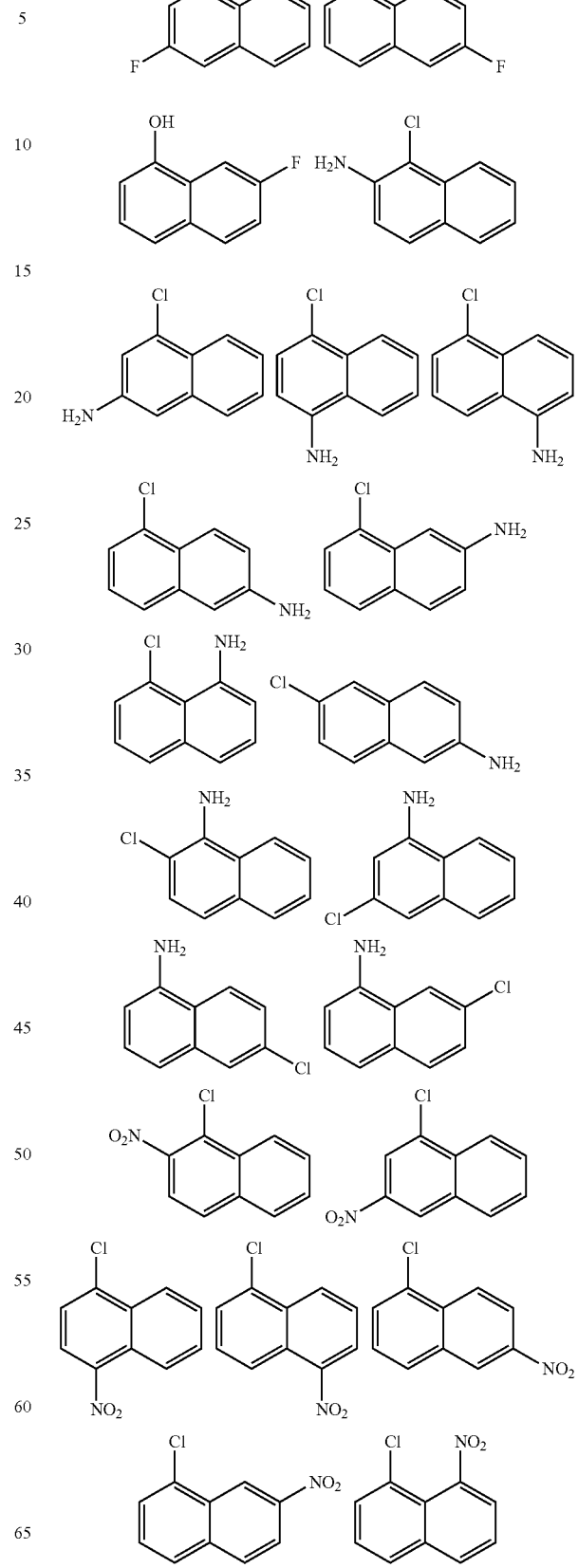

-continued
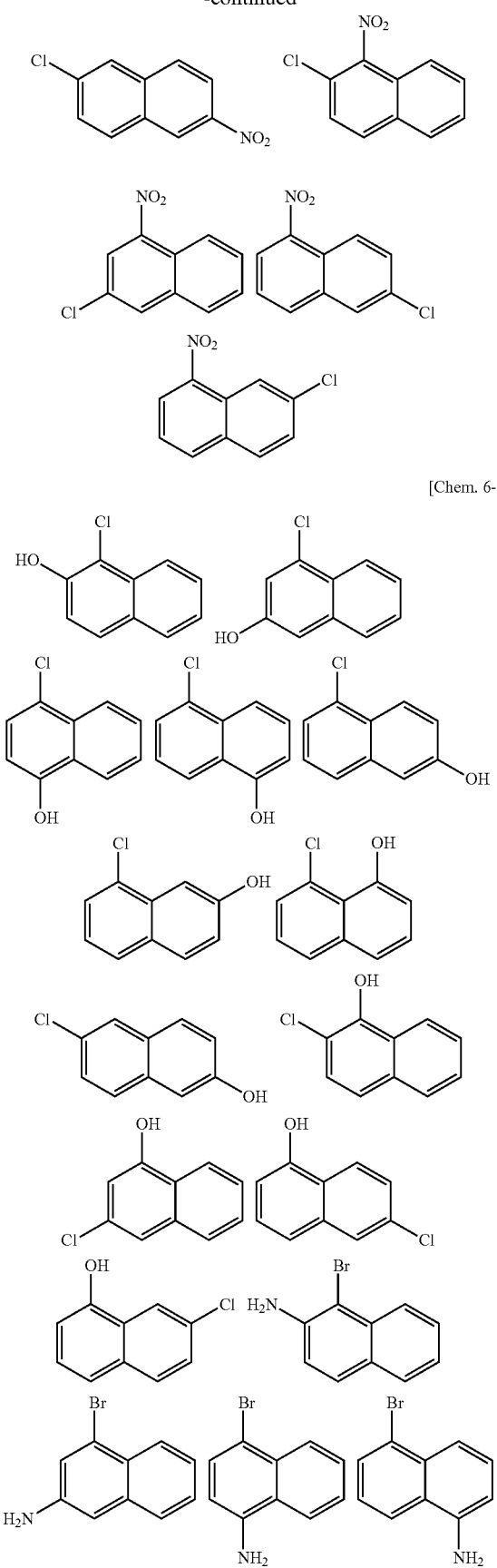
[Chem. 6-5]
-continued
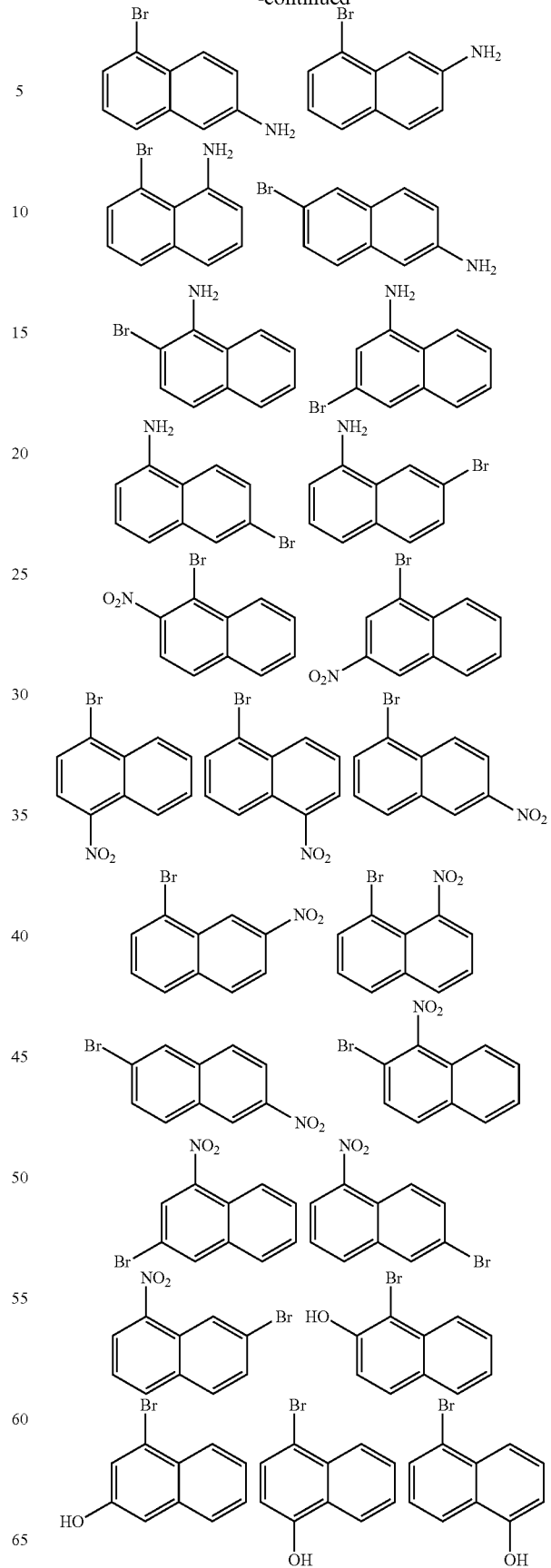

-continued
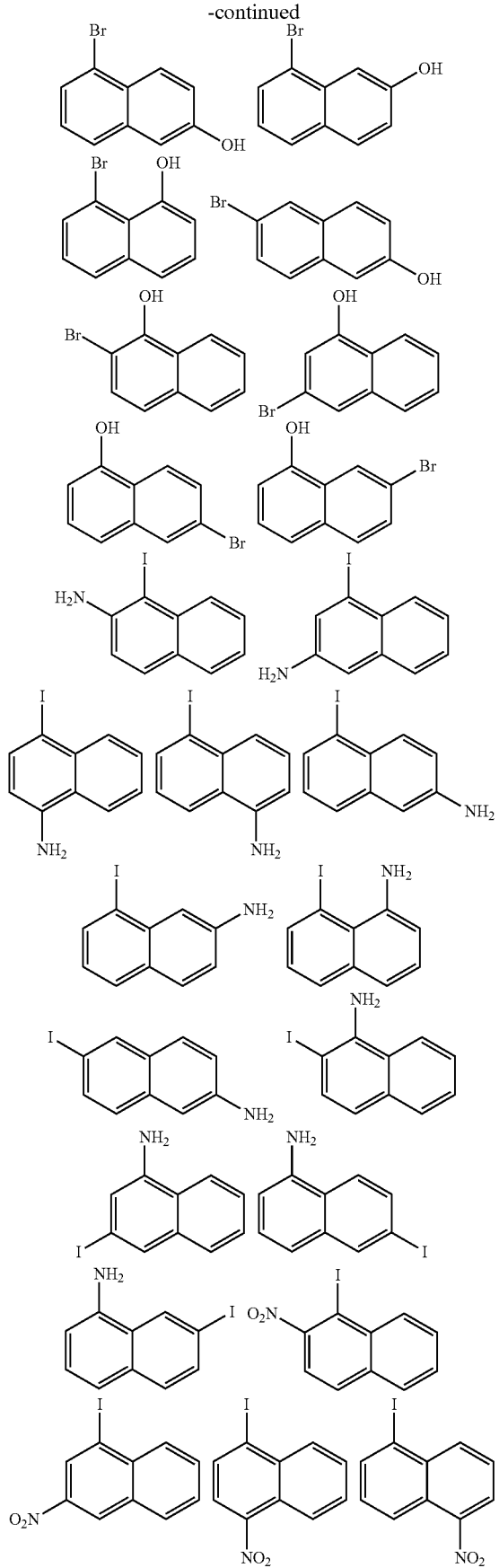
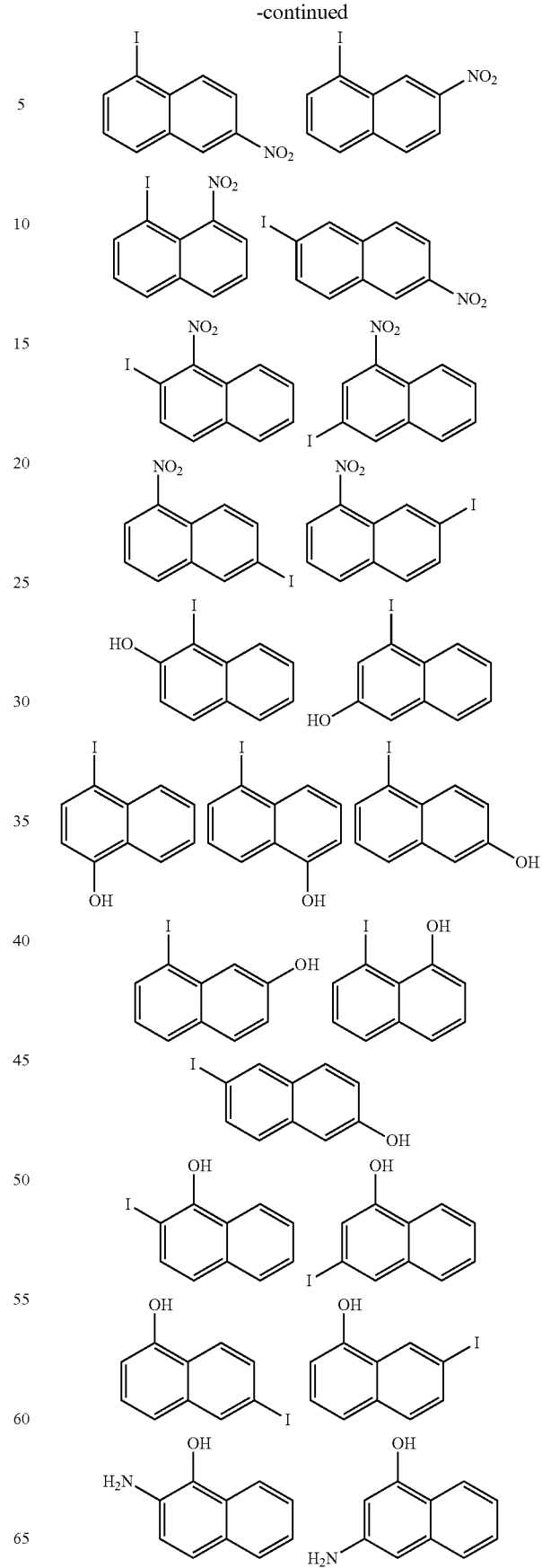

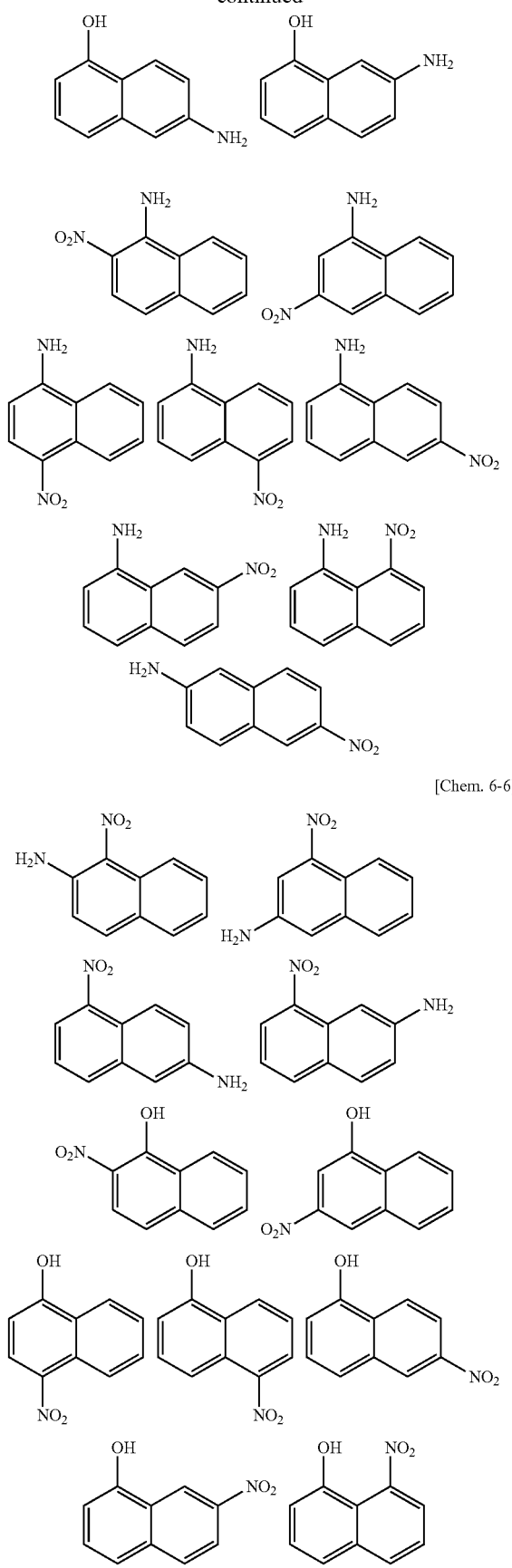
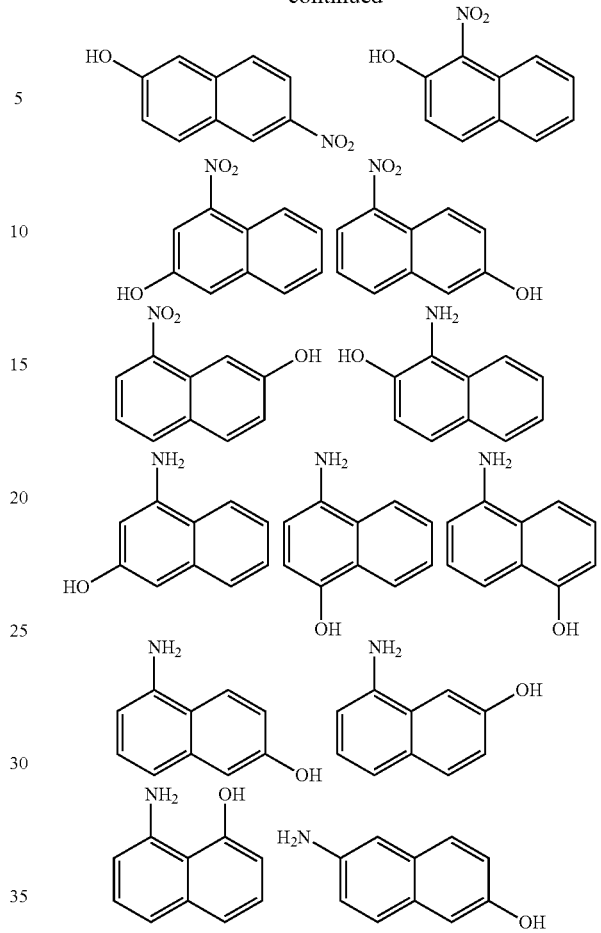

The following description will discuss production processes [D] through [S] as examples of the above described processes which are part of the process for producing the compound of the formula (II), the formula (III), the formula (IV), or the formula (VIII).

<Nitration Process>
Production Process [D]

In the production process [D], a compound represented by a formula (IX-I) is caused to react (nitration reaction) with a nitrating agent so as to produce a compound represented by a formula (X-I).

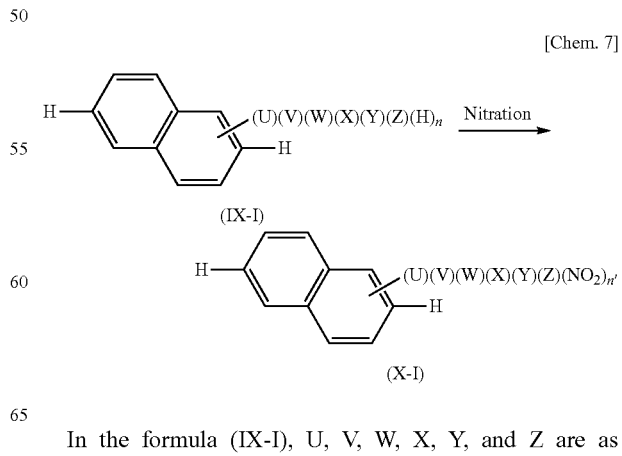

In the formula (IX-I), U, V, W, X, Y, and Z are as described above. Among these substituent groups, at least one substituent group is a hydrogen atom, and n represents the number of substituent groups which are hydrogen atoms among the U, V, W, X, Y, and Z and is an integer satisfying 1≤n≤6. In the formula (X-I), U, V, W, X, Y, and Z are as described above. Among these substituent groups, at least one substituent group is a nitro group, and n' is an integer satisfying 1≤n'≤n.

Therefore, for example, in a case where Y and Z in the formula (IX-I) are hydrogen atoms, the portion of the substituent groups in the formula (IX-I) is indicated by "—(U)(V)(W)(X)(H)$_2$" and, in a case where U, V, W and X are hydrogen atoms, the portion of the substituent groups is indicated by "—(Y)(Z)(H)$_4$". Note, however, that substitution positions of the U, V, W, X, Y, and Z in the naphthalene ring are not particularly determined, specifically, a structure in which Y and Z in the formula (IX-I) are hydrogen atoms indicates that, among the six substituent groups which bind to the naphthalene ring and are not the originally binding two hydrogen atoms, two substituent groups are hydrogen atoms, and four substituent groups are substituent groups other than hydrogen atoms. Moreover, a structure in which U, V, W, and X are hydrogen atoms indicates that, among the six substituent groups which bind to the naphthalene ring and are not the originally binding two hydrogen atoms, four substituent groups are hydrogen atoms, and two substituent groups are substituent groups other than hydrogen atoms. Further, for example, a structure in which Y and Z in the formula (X-I) are nitro groups indicates that, among the six substituent groups which bind to the naphthalene ring and are not the originally binding two hydrogen atoms, two substituent groups are nitro groups, and four substituent groups are substituent groups other than nitro groups (if n'<n, hydrogen atoms which have not been nitrated are also included).

In the processes which are part of the process for producing the compound of the formula (II), the formula (III), the formula (IV), or the formula (VIII), substituent groups other than substituent groups (e.g., hydrogen atoms in the production process [D]) which are to be reacted are selected from substituent groups that are not involved in the reaction so that no side reaction would occur. The substituent groups to be selected are preferably different from substituent groups that are generated as a result of the reaction.

In the descriptions below, also in the later-described other formulae including U, V, W, X, Y, and Z, descriptions such as "—(U)(V)(W)(X)(Y)(Z)(oo)$_n$," and "—(U)(V)(W)(X)(Y)(Z)(oo)$_{n'}$," represent structures similar to those described above, unless otherwise specified. Moreover, substituent groups other than substituent groups to be reacted are assumed to be selected from substituent groups which are not involved in the reaction.

The nitrating agent is not limited to a particular one, provided that the reaction proceeds with use of the nitrating agent. Examples of the nitrating agent include a nitrating material constituted by a combination of potassium nitrate/concentrated nitric acid or fuming nitric acid/concentrated sulfuric acid or fuming nitric acid/acetic anhydride, and the like. The nitrating agent can be used in an equivalent weight of 1 to 20, with respect to 1 equivalent weight of the compound of the formula (IX-I).

The reaction in the production process [D] can be carried out, optionally, in the presence of a solvent. The solvent is not limited to a particular one, provided that the reaction proceeds with use of the solvent. Examples of the solvent include the solvents for use in the first step of the production process [A].

A reaction temperature is typically −30° C. to 100° C., preferably 0° C. to 50° C. A reaction time is typically 1 hour to 48 hours.

Production Process [E]

In the production process [E], a compound represented by a formula (IX-II) is caused to react (oxidation reaction) with an oxidizer so as to produce a compound represented by a formula (X-II).

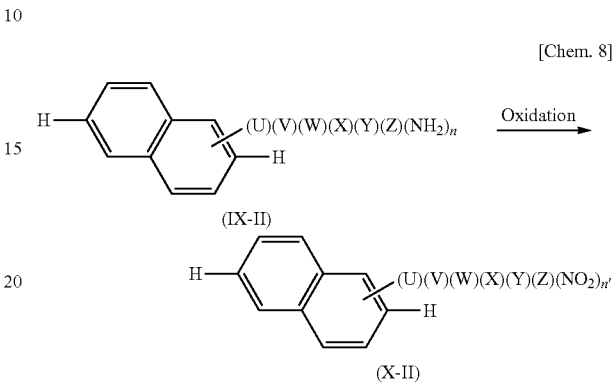

[Chem. 8]

In the formula (IX-II), U, V, W, X, Y, and Z are as described above. Among these substituent groups, at least one substituent group is an amino group, and n represents the number of substituent groups which are amino groups among the U, V, W, X, Y, and Z and is an integer satisfying 1≤n≤6. In the formula (X-II), U, V, W, X, Y, and Z are as described above. Among these substituent groups, at least one substituent group is a nitro group, and n' is an integer satisfying 1≤n'≤n.

The oxidizer is not limited to a particular one, provided that the reaction proceeds with use of the oxidizer. Examples of the oxidizer include oxygen gas, ozone gas, hydrogen peroxide, m-chloroperbenzoic acid, tert-butylhydroperoxide, sodium perborate, dimethyldioxirane, and the like. The oxidizer can be used in an equivalent weight of 1 to 20, preferably in an equivalent weight of 1 to 5, with respect to 1 equivalent weight of the compound of the formula (IX-II).

The reaction in the production process [E] can be carried out, typically, in the presence of a solvent. The solvent is not limited to a particular one, provided that the reaction proceeds with use of the solvent. Examples of the solvent include the solvents for use in the first step of the production process [A].

Moreover, the reaction in the production process [E] can be carried out, optionally, in the presence of a catalyst. The catalyst is not limited to a particular one, provided that the reaction proceeds with use of the catalyst. Examples of the catalyst include methyltrioxorhenium, zirconium tert-butoxide, and the like. The catalyst can be used in an equivalent weight of 0.0001 to 5, with respect to 1 equivalent weight of the compound of the formula (IX-II).

A reaction temperature is typically 0° C. to 120° C., preferably 0° C. to 50° C. A reaction time is typically 1 hour to 48 hours.

<Halogenation and Halogen Substitution Processes>

Production Process [F]

In the production process [F], a compound of a formula (IX-III) is caused to react (halogenation reaction) with a halogenating agent so as to produce a compound represented by a formula (X-III).

[Chem. 9]

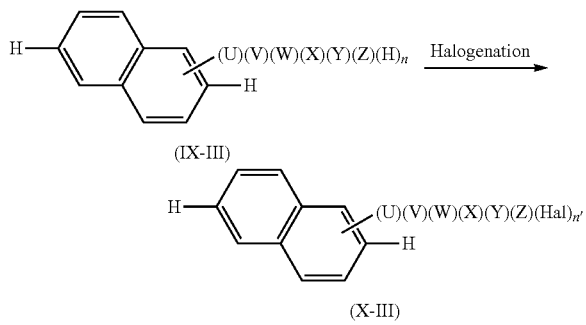

In the formula (IX-III), U, V, W, X, Y, and Z are as described above. Among these substituent groups, at least one substituent group is a hydrogen atom, and n represents the number of substituent groups which are hydrogen atoms among the U, V, W, X, Y, and Z and is an integer satisfying $1 \le n \le 6$. In the formula (X-III), U, V, W, X, Y, and Z are as described above. Among these substituent groups, at least one substituent group is a halogen atom (Hal), and n' is an integer satisfying $1 \le n' \le n$.

The halogenating agent is not limited to a particular one, provided that the reaction proceeds with use of the halogenating agent. Examples of the halogenating agent include the halogenating agents for use in the third step of the production process [A]. The halogenating agent can be used in an equivalent weight of 1 to 20, preferably in an equivalent weight of 1 to 5, with respect to 1 equivalent weight of the compound of the formula (IX-III).

The reaction in the production process [F] can be carried out, typically, in the presence of a solvent. The solvent is not limited to a particular one, provided that the reaction proceeds with use of the solvent. Examples of the solvent include the solvents for use in the first step of the production process [A].

A reaction temperature is typically 0° C. to 200° C., preferably 0° C. to 120° C. A reaction time is typically 1 hour to 48 hours.

Production Process [G]

In the production process [G], a compound represented by a formula (IX-IV) is caused to react (diazotization reaction) with inorganic nitrite or nitrous ester to obtain a diazonium compound, and then the diazonium compound is caused to react (halogenation reaction) with a halogenating agent so as to produce a compound represented by a formula (X-IV).

[Chem. 10]

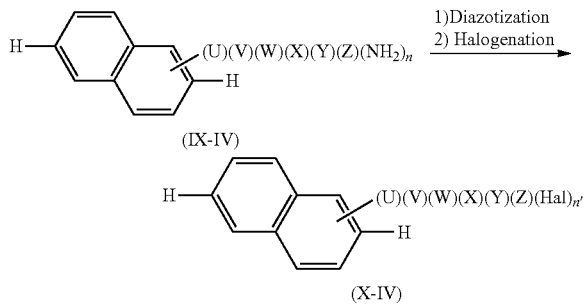

In the formula (IX-IV), U, V, W, X, Y, and Z are as described above. Among these substituent groups, at least one substituent group is an amino group, and n represents the number of substituent groups which are amino groups among the U, V, W, X, Y, and Z and is an integer satisfying $1 \le n \le 6$. In the formula (X-IV), U, V, W, X, Y, and Z are as described above. Among these substituent groups, at least one substituent group is a halogen atom (Hal), and n' is an integer satisfying $1 \le n' \le n$.

The inorganic nitrite is not limited to a particular one, provided that the reaction proceeds with use of the inorganic nitrite. Examples of the inorganic nitrite include sodium nitrite, potassium nitrite, and the like. The nitrous ester is not limited to a particular one, provided that the reaction proceeds with use of the nitrous ester. Examples of the nitrous ester include tert-butyl nitrite, isoamyl nitrite, and the like. The inorganic nitrite or nitrous ester can be used in an equivalent weight of 1 to 20, preferably in an equivalent weight of 1 to 5, with respect to 1 equivalent weight of the compound of the formula (IX-IV).

The halogenating agent is not limited to a particular one, provided that the reaction proceeds with use of the halogenating agent. Examples of the halogenating agent include fluorine, chlorine, bromine, iodine; potassium halide such as potassium iodide; copper(I) halide salts such as copper(I) fluoride, copper(I) chloride, copper(I) bromide, and copper (I) iodide; copper(II) halide salts such as copper(II) fluoride, copper(II) chloride, copper(II) bromide, and copper(II) iodide; hydrohalogenic acids such as hydrofluoric acid, hydrochloric acid, hydrobromic acid, and hydroiodic acid; tetrafluoroboric acid, silver tetrafluoroborate; and the like. The halogenating agent can be used in an equivalent weight of 1 to 20, preferably in an equivalent weight of 1 to 5, with respect to 1 equivalent weight of the compound of the formula (IX-IV).

The reaction in the production process [G] can be carried out, typically, in the presence of a solvent. The solvent is not limited to a particular one, provided that the reaction proceeds with use of the solvent. Examples of the solvent include the solvents for use in the first step of the production process [A].

Moreover, the diazotization reaction in the production process [G] can be carried out, optionally, in the presence of a copper catalyst, acid, or base.

The copper catalyst is not limited to a particular one, provided that the reaction proceeds with use of the copper catalyst. Examples of the copper catalyst include the copper (I) halide salt, the copper(II) halide salt, copper(I) oxide, copper(II) sulfate pentahydrate, and the like. The copper catalyst can be used in an equivalent weight of 0.01 to 5, with respect to 1 equivalent weight of the compound of the formula (IX-IV).

The acid is not limited to a particular one, provided that the reaction proceeds with use of the acid. Examples of the acid include inorganic acids such as hydrochloric acid and sulfuric acid; organic acids such as acetic acid and methanesulfonic acid; and the like. The acid can be used in an equivalent weight of 1 to 20, with respect to 1 equivalent weight of the compound of the formula (IX-IV).

The base is not limited to a particular one, provided that the reaction proceeds with use of the base. Examples of the base include alkali metal hydride such as sodium hydride; alkali metal carbonate such as sodium carbonate, potassium carbonate, and cesium carbonate; alkali metal hydroxide such as lithium hydroxide, sodium hydroxide, and potassium hydroxide; and the like. The base can be used in an equivalent weight of 1 to 20, with respect to 1 equivalent weight of the compound of the formula (IX-IV).

A reaction temperature in the production process [G] is typically −20° C. to 200° C. A reaction time is typically 1 hour to 48 hours.

Production Process [H]

In the production process [H], a compound of a formula (IX-V) is caused to react (halogen substitution reaction) with a halogen substituting agent so as to produce a compound represented by a formula (X-V).

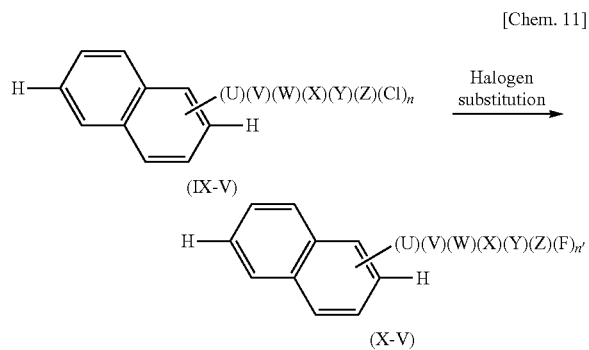

[Chem. 11]

In the formula (IX-V), U, V, W, X, Y, and Z are as described above. Among these substituent groups, at least one substituent group is a chlorine atom, and n represents the number of substituent groups which are chlorine atoms among the U, V, W, X, Y, and Z and is an integer satisfying $1 \leq n \leq 6$. In the formula (X-IV), U, V, W, X, Y, and Z are as described above. Among these substituent groups, at least one substituent group is a fluorine atom, and n' is an integer satisfying $1 \leq n' \leq n$.

The halogen substituting agent can be, for example, cesium fluoride or the like. The halogen substituting agent can be used in an equivalent weight of 1 to 20, preferably in an equivalent weight of 1 to 5, with respect to 1 equivalent weight of the compound of the formula (IX-V).

The reaction in the production process [H] can be carried out, typically, in the presence of a solvent. The solvent is not limited to a particular one, provided that the reaction proceeds with use of the solvent. Examples of the solvent include the solvents for use in the production process [G].

A reaction temperature is typically −20° C. to 200° C. A reaction time is typically 1 hour to 48 hours.

Production Process [I]

In the production process [I], a compound of a formula (IX-VI) is caused to react (halogenation reaction) with a halogenating agent so as to produce a compound represented by a formula (X-VI).

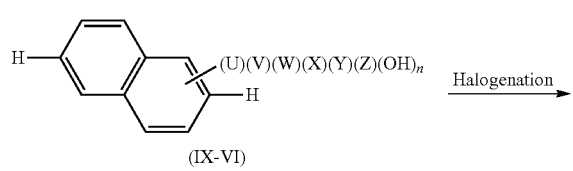

[Chem. 12]

In the formula (IX-VI), U, V, W, X, Y, and Z are as described above. Among these substituent groups, at least one substituent group is a hydroxy group, and n represents the number of substituent groups which are hydroxy groups among the U, V, W, X, Y, and Z and is an integer satisfying $1 \leq n \leq 6$. In the formula (X-VI), U, V, W, X, Y, and Z are as described above. Among these substituent groups, at least one substituent group is a fluorine atom, and n' is an integer satisfying $1 \leq n' \leq n$.

The halogenating agent is not limited to a particular one, provided that the reaction proceeds with use of the halogenating agent. Examples of the halogenating agent include cesium fluoride and the like. Alternatively, it is possible to use a commercially available halogenating agent (manufactured by SIGMA-ALDRICH; product name: PhenoFluor). The halogenating agent can be used in an equivalent weight of 1 to 20, preferably in an equivalent weight of 1 to 5, with respect to 1 equivalent weight of the compound of the formula (IX-VI).

The reaction in the production process [I] can be carried out, typically, in the presence of a solvent. The solvent is not limited to a particular one, provided that the reaction proceeds with use of the solvent. Examples of the solvent include the solvents for use in the first step of the production process [A].

A reaction temperature is typically 0° C. to 200° C., preferably 0° C. to 120° C. A reaction time is typically 1 hour to 48 hours.

Production Process [J]

In the production process [J], a compound of a formula (IX-VII) is caused to react (halogenation reaction) with a halogenating agent so as to produce a compound represented by a formula (X-VII).

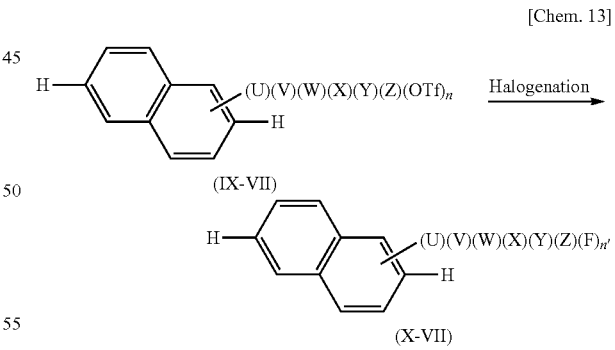

[Chem. 13]

In the formula (IX-VII), U, V, W, X, Y, and Z are as described above. Among these substituent groups, at least one substituent group is a trifluoromethanesulfonyl group (OTf), and n represents the number of substituent groups which are trifluoromethanesulfonyl groups among the U, V, W, X, Y, and Z and is an integer satisfying $1 \leq n \leq 6$. In the formula (X-VII), U, V, W, X, Y, and Z are as described above. Among these substituent groups, at least one substituent group is a fluorine atom, and n' is an integer satisfying $1 \leq n' \leq n$.

The halogenating agent is not limited to a particular one, provided that the reaction proceeds with use of the halogenating agent. Examples of the halogenating agent include cesium fluoride and the like. The halogenating agent can be used in an equivalent weight of 1 to 20, preferably in an equivalent weight of 1 to 5, with respect to 1 equivalent weight of the compound of the formula (IX-VII).

The reaction in the production process [J] can be carried out, typically, in the presence of a solvent, a metal catalyst, and a ligand.

The solvent is not limited to a particular one, provided that the reaction proceeds with use of the solvent. Examples of the solvent include the solvents for use in the first step of the production process [A].

The metal catalyst is not limited to a particular one, provided that the reaction proceeds with use of the metal catalyst. Examples of the metal catalyst include palladium catalysts such as palladium($\pi$-cinnamyl)chloride, bis(triphenylphosphine)palladiumdichloride, tetrakis(triphenylphosphine)palladium, [1,1'-bis(diphenylphosphino)ferrocene]palladium(II)dichloride, and bis(tri-tert-butylphosphine)palladium, and the like.

Examples of the ligand include 2-(dicyclohexylphosphino)-3,6-dimethoxy-2',4',6'-triisopropyl-1,1'-biphenyl and the like. Alternatively, it is possible to use a commercially available ligand (manufactured by SIGMA-ALDRICH; product name: AdBrettPhos).

Each of the metal catalyst and the ligand can be used in an equivalent weight of 0.01 to 5, preferably in an equivalent weight of 0.05 to 1, with respect to 1 equivalent weight of the compound of the formula (IX-VII).

A reaction temperature is typically 0° C. to 200° C., preferably 0° C. to 120° C. A reaction time is typically 1 hour to 48 hours.

Production Process [K]

In the production process [K], a compound of a formula (IX-VIII) is caused to react (halogenation reaction) with a halogenating agent so as to produce a compound represented by a formula (X-VIII).

[Chem. 14]

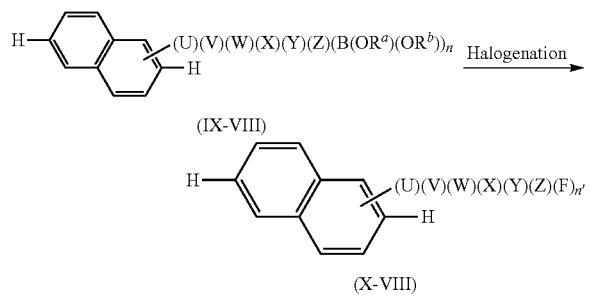

In the formula (IX-VIII), U, V, W, X, Y, and Z are as described above. Among these substituent groups, at least one substituent group is a $B(OR^a)(OR^b)$ group, each of $R^a$ and $R^b$ is independently a hydrogen atom or a $C_1$-$C_{10}$ alkyl group, ($OR^a$) and ($OR^b$) can form a ring together, and n represents the number of substituent groups which are $B(OR^a)(OR^b)$ groups among the U, V, W, X, Y, and Z and is an integer satisfying 1≤n≤6. In the formula (X-VIII), U, V, W, X, Y, and Z are as described above. Among these substituent groups, at least one substituent group is a fluorine atom, and n' is an integer satisfying 1≤n'≤n.

Specific examples of the $B(OR^a)(OR^b)$ group include a boronic acid group, a boronic acid dimethyl ester group, a boronic acid diethyl ester group, a boronic acid dipropyl ester group, a boronic acid diisopropyl ester group, a boronic acid dibutyl ester group, a boronic acid dihexyl ester group, a boronic acid pinacol ester group, a boronic acid neopentyl glycol ester group, a boronic acid hexylene glycol ester group, a boronic acid catechol ester group, a boronic acid ethylene glycol ester group, a boronic acid propylene glycol ester group, a boronic acid 1,3-propanediol ester group, a boronic acid 1,3-butanediol ester group, and the like.

The halogenating agent is not limited to a particular one, provided that the reaction proceeds with use of the halogenating agent. Examples of the halogenating agent include 1-chloromethyl-4-fluoro-1,4-diazoniabicyclo[2.2.2]octane-bis(tetrafluoroborate), N-fluorobenzenesulfonimide, 1-fluoropyridinium triflate, 2,6-dicyclo-1-fluoropyridinium triflate, 1-fluoro-2,4,6-trimethylhexafluorophosphate, and the like. The halogenating agent can be used in an equivalent weight of 1 to 20, preferably in an equivalent weight of 1 to 5, with respect to 1 equivalent weight of the compound of the formula (IX-VIII).

The reaction in the production process [K] can be carried out, typically, in the presence of a solvent or metal salt.

The solvent is not limited to a particular one, provided that the reaction proceeds with use of the solvent. Examples of the solvent include the solvents for use in the first step of the production process [A].

The metal salt is not limited to a particular one, provided that the reaction proceeds with use of the metal salt. Examples of the metal salt include silver(I) fluoride, copper (I) triflate, bis(pivaloylnitrile)copper(I) triflate, and the like. The metal salt can be used in an equivalent weight of 1 to 20, preferably in an equivalent weight of 1 to 5, with respect to 1 equivalent weight of the compound of the formula (IX-VIII).

A reaction temperature is typically 0° C. to 200° C., preferably 0° C. to 120° C. A reaction time is typically 1 hour to 48 hours.

<Boronization Process>

Production Process [L]

In the production process [L], a compound represented by a formula (IX-IX) is caused to react (lithiation reaction) with organolithium to obtain an aryllithium compound, and then the aryllithium compound is caused to react (boronization reaction) with a boronizing agent so as to produce a compound represented by a formula (X-IX).

[Chem. 15]

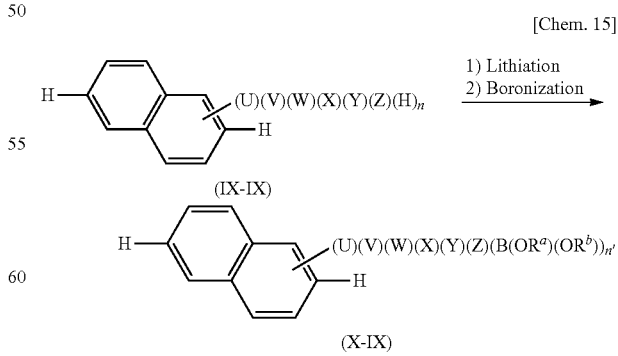

In the formula (IX-IX), U, V, W, X, Y, and Z are as described above. Among these substituent groups, at least one substituent group is a hydrogen atom, and n represents the number of substituent groups which are hydrogen atoms among the U, V, W, X, Y, and Z and is an integer satisfying 1≤n≤6. In the formula (X-IX), U, V, W, X, Y, and Z are as described above. Among these substituent groups, at least one substituent group is a B(OR$^a$)(OR$^b$) group, each of R$^a$ and R$^b$ is independently a hydrogen atom or a C$_1$-C$_{10}$ alkyl group, (OR$^a$) and (OR$^b$) can form a ring together, and n' is an integer satisfying 1≤n'≤n.

Specific examples of the B(OR$^a$)(OR$^b$) group include the substituent groups exemplified in the production process [K].

The organolithium is not limited to a particular one, provided that the reaction proceeds with use of the organolithium. Examples of the organolithium include n-butyllithium, lithium diisopropylamide, and the like. The organolithium can be used in an equivalent weight of 1 to 20, with respect to 1 equivalent weight of the compound of the formula (IX-IX).

The boronizing agent is not limited to a particular one, provided that the reaction proceeds with use of the boronizing agent. Examples of the boronizing agent include trimethyl borate, triethyl borate, triisopropyl borate, 4,4,4',4',5,5,5',5'-octamethyl-2,2'-bi-1,3,2-dioxaborolane, 2-isopropoxy-4,4,5,5-tetramethyl-1,3,2-dioxaborolane, and the like. The boronizing agent can be used in an equivalent weight of 1 to 20, with respect to 1 equivalent weight of the compound of the formula (IX-IX).

The reaction in the production process [L] can be carried out, typically, in the presence of a solvent. The solvent is not limited to a particular one, provided that the reaction proceeds with use of the solvent. Examples of the solvent include the solvents for use in the first step of the production process [A].

A reaction temperature is typically –80° C. to 120° C. A reaction time is typically 1 hour to 48 hours.

Production Process [M]

In the production process [M], a compound represented by a formula (IX-X) is reacted (boronization reaction) with a boronizing agent so as to produce a compound represented by a formula (X-X).

[Chem. 16]

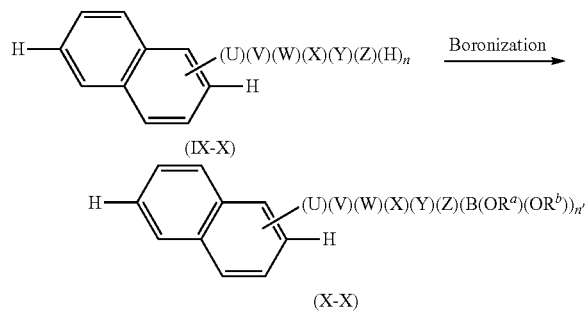

In the formula (IX-X), U, V, W, X, Y, and Z are as described above. Among these substituent groups, at least one substituent group is a hydrogen atom, and n represents the number of substituent groups which are hydrogen atoms among the U, V, W, X, Y, and Z and is an integer satisfying 1≤n≤6. In the formula (X-X), U, V, W, X, Y, and Z are as described above. Among these substituent groups, at least one substituent group is a B(OR$^a$)(OR$^b$) group, each of R$^a$ and R$^b$ is independently a hydrogen atom or a C$_1$-C$_{10}$ alkyl group, (OR$^a$) and (OR$^b$) can form a ring together, and n' is an integer satisfying 1≤n'≤n.

Specific examples of the B(OR$^a$)(OR$^b$) group include the substituent groups exemplified in the production process [K].

The boronizing agent is not limited to a particular one, provided that the reaction proceeds with use of the boronizing agent. Examples of the boronizing agent include 4,4,5,5-tetramethyl-1,3,2-dioxaborolane and the like. The boronizing agent can be used in an equivalent weight of 1 to 20, preferably in an equivalent weight of 1 to 5, with respect to 1 equivalent weight of the compound of the formula (IX-X).

The reaction in the production process [M] can be carried out typically in the presence of a solvent, an organic metal catalyst, an organic ligand, and a base.

The solvent is not limited to a particular one, provided that the reaction proceeds with use of the solvent. Examples of the solvent include the solvents for use in the first step of the production process [A].

The organic metal catalyst is not limited to a particular one, provided that the reaction proceeds with use of the organic metal catalyst. Examples of the organic metal catalyst include the organic metal catalysts for use in the second step of the production process [B]. The organic metal catalyst can be used in an equivalent weight of 0.001 to 5, preferably in an equivalent weight of 0.01 to 1, with respect to 1 equivalent weight of the compound of the formula (IX-X).

The organic ligand is not limited to a particular one, provided that the reaction proceeds with use of the organic ligand. Examples of the organic ligand include the organic ligands for use in the third step of the production process [A]. The organic ligand can be used in an equivalent weight of 0.001 to 5, preferably in an equivalent weight of 0.01 to 1, with respect to 1 equivalent weight of the compound of the formula (IX-X).

The base is not limited to a particular one, provided that the reaction proceeds with use of the base. Examples of the base include the bases for use in the first step of the production process [A]. The base can be used in an equivalent weight of 1 to 20, preferably in an equivalent weight of 1 to 5, with respect to 1 equivalent weight of the compound of the formula (IX-X).

A reaction temperature is typically 0° C. to 120° C. A reaction time is typically 1 hour to 48 hours.

Production Process [N]

In the production process [N], a compound represented by a formula (IX-XI) is caused to react (boronization reaction) with a boronizing agent so as to produce a compound represented by a formula (X-XI).

[Chem. 17]

In the formula (IX-XI), U, V, W, X, Y, and Z are as described above. Among these substituent groups, at least one substituent group is a halogen atom (Hal), and n represents the number of substituent groups which are halogen atoms among the U, V, W, X, Y, and Z and is an integer satisfying 1≤n≤6. In the formula (X-XI), U, V, W, X, Y, and Z are as described above. Among these substituent groups, at least one substituent group is a B(OR$^a$)(OR$^b$) group, each of R$^a$ and R$^b$ is independently a hydrogen atom or a C$_1$-C$_{10}$ alkyl group, (OR$^a$) and (OR$^b$) can form a ring together, and n' is an integer satisfying 1≤n'≤n.

Specific examples of the B(OR$^a$)(OR$^b$) group include the substituent groups exemplified in the production process [K].

The boronizing agent is not limited to a particular one, provided that the reaction proceeds with use of the boronizing agent. Examples of the boronizing agent include 4,4,5,5-tetramethyl-1,3,2-dioxaborolane and the like. The boronizing agent can be used in an equivalent weight of 1 to 20, preferably in an equivalent weight of 1 to 5, with respect to 1 equivalent weight of the compound of the formula (IX-XI).

The reaction in the production process [N] can be carried out typically in the presence of a solvent, an organic metal catalyst, an organic ligand, and a base.

The solvent is not limited to a particular one, provided that the reaction proceeds with use of the solvent. Examples of the solvent include the solvents for use in the first step of the production process [A].

The organic metal catalyst is not limited to a particular one, provided that the reaction proceeds with use of the organic metal catalyst. Examples of the organic metal catalyst include the organic metal catalysts for use in the second step of the production process [B]. The organic metal catalyst can be used in an equivalent weight of 0.001 to 5, preferably in an equivalent weight of 0.01 to 1, with respect to 1 equivalent weight of the compound of the formula (IX-XI).

The organic ligand is not limited to a particular one, provided that the reaction proceeds with use of the organic ligand. Examples of the organic ligand include the organic ligands for use in the third step of the production process [A]. The organic ligand can be used in an equivalent weight of 0.001 to 5, preferably in an equivalent weight of 0.01 to 1, with respect to 1 equivalent weight of the compound of the formula (IX-XI).

The base is not limited to a particular one, provided that the reaction proceeds with use of the base. Examples of the base include the bases for use in the first step of the production process [A]. The base can be used in an equivalent weight of 1 to 20, preferably in an equivalent weight of 1 to 5, with respect to 1 equivalent weight of the compound of the formula (IX-XI).

A reaction temperature is typically 0° C. to 120° C. A reaction time is typically 1 hour to 48 hours.

<Hydroxylation Process and Protection and Deprotection Processes>

Production Process [O]

In the production process [O], a compound represented by a formula (IX-XII) is caused to react (hydroxylation reaction) with a hydroxylating agent so as to produce a compound represented by a formula (X-XII).

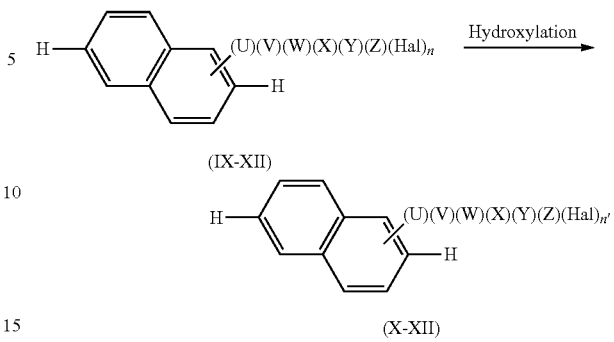

[Chem. 18]

In the formula (IX-XII), U, V, W, X, Y, and Z are as described above. Among these substituent groups, at least one substituent group is a halogen atom (Hal), and n represents the number of substituent groups which are halogen atoms (Hal) among the U, V, W, X, Y, and Z and is an integer satisfying 1≤n≤6. In the formula (X-XII), U, V, W, X, Y, and Z are as described above. Among these substituent groups, at least one substituent group is a hydroxy group, and n' is an integer satisfying 1≤n'≤n.

The hydroxylating agent is not limited to a particular one, provided that the reaction proceeds with use of the hydroxylating agent. Examples of the hydroxylating agent include metal hydroxide such as lithium hydroxide, sodium hydroxide, potassium hydroxide, and cesium hydroxide; tetrabutylammonium hydroxide, tetrabutylammonium bromide hydroxide, tetrabutylammonium iodide hydroxide; and the like. The hydroxylating agent can be used in an equivalent weight of 1 to 20, preferably in an equivalent weight of 1 to 5, with respect to 1 equivalent weight of the compound of the formula (IX-XII).

The reaction in the production process [O] can be typically carried out in the presence of a solvent and, optionally, in the presence of a copper compound, an organic ligand, and a phase transfer catalyst.

The solvent is not limited to a particular one, provided that the reaction proceeds with use of the solvent. Examples of the solvent include the solvents for use in the first step of the production process [A].

The copper compound is not limited to a particular one, provided that the reaction proceeds with use of the copper compound. Examples of the copper compound include copper(I) halide salts such as copper(I) fluoride, copper(I) chloride, copper(I) bromide, and copper(I) iodide; copper (II) halide salts such as copper(II) fluoride, copper(II) chloride, copper(II) bromide, and copper(II) iodide; copper(I) oxide, copper(II) oxide; copper(II) sulfate pentahydrate; and the like. The copper compound can be used in an equivalent weight of 1 to 20, preferably in an equivalent weight of 1 to 5, with respect to 1 equivalent weight of the compound of the formula (IX-XII).

The organic ligand is not limited to a particular one, provided that the reaction proceeds with use of the organic ligand. Examples of the organic ligand include the organic ligands for use in the third step of the production process [A]. The organic ligand can be used in an equivalent weight of 0.001 to 5, preferably in an equivalent weight of 0.01 to 1, with respect to 1 equivalent weight of the compound of the formula (IX-XII).

The phase transfer catalyst is not limited to a particular one, provided that the reaction proceeds with use of the phase transfer catalyst. Examples of the phase transfer catalyst include the phase transfer catalysts for use in the first step of the production process [A]. The phase transfer catalyst can be used in an equivalent weight of 1 to 20, preferably in an equivalent weight of 1 to 5, with respect to 1 equivalent weight of the compound of the formula (IX-XII).

A reaction temperature is typically 0° C. to 200° C., preferably 0° C. to 120° C. A reaction time is typically 1 hour to 48 hours.

With respect to the introduced hydroxy group, it is possible to optionally carry out introduction of a protective group and cleavage (deprotection reaction) of the protective group. A protective group suitable for protection of a hydroxy group, a method for introducing the protective group, and a method for cleaving the protective group are known to a person skilled in the art (for example, see Protective Groups in Organic Synthesis, fourth edition, 2006, John Wiley & Sons, INC.)

The protective group for the hydroxy group encompasses all groups which can be used as protective groups for ordinary hydroxy groups. Specific examples of such groups include groups described in Protective Groups in Organic Synthesis, fourth edition, 2006, John Wiley & Sons, INC., and the like. Specific examples of the protective group include a benzyl group that can be substituted by a substituent group selected from a halogen atom, a $C_1$-$C_6$ alkoxy group, and a nitro group (e.g., benzyl group, p-methoxybenzyl group, p-nitrobenzyl group, p-chlorobenzyl group, or the like); a $C_1$-$C_6$ alkoxycarbonyl group that can be substituted by one to three substituent groups selected from a halogen atom and an aryl group (e.g., methoxycarbonyl group, tert-butoxycarbonyl group, 2,2,2-trichloroethoxy carbonyl group, benzyloxycarbonyl group, 9-fluorenylmethoxycarbonyl group, or the like); an allyl group; dialkylaminoalkylidene group (e.g., N,N-dimethylaminomethylene group, N,N-diethylaminomethylene group, or the like); a formyl group; a $C_1$-$C_6$ alkanoyl group that can be substituted by one to three halogen atoms (e.g., acetyl group, chloroacetyl group, trichloroacetyl group, trifluoroacetyl group, or pivaloyl group); a benzoyl group; a silyl group having three substituent groups which are identical with each other or different from each other and are selected from a $C_1$-$C_6$ alkyl group and an aryl group (e.g., trimethylsilyl group, triethylsilyl group, tert-butyldimethylsilyl group, tert-butyldiphenylsilyl group, or the like); and the like.

<Amination Process and Protection and Deprotection Processes>

Production Process [P]

In the production process [P], a compound represented by a formula (IX-XIII) is caused to react (amination reaction) with an aminating agent so as to produce a compound represented by a formula (X-XIII).

[Chem. 19]

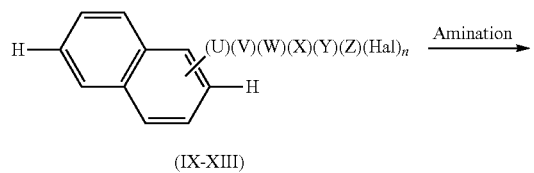

(IX-XIII)

(X-XIII)

In the formula (IX-XIII), U, V, W, X, Y, and Z are as described above. Among these substituent groups, at least one substituent group is a halogen atom (Hal), and n represents the number of substituent groups which are halogen atoms (Hal) among the U, V, W, X, Y, and Z and is an integer satisfying 1≤n≤6. In the formula (X-XIII), U, V, W, X, Y, and Z are as described above. Among these substituent groups, at least one substituent group is an amino group, and n' is an integer satisfying 1≤n'≤n.

The aminating agent is not limited to a particular one, provided that the reaction proceeds with use of the aminating agent. Examples of the aminating agent include ammonia, ammonia water, ammonium hydroxide, tetrabutylammonium hydroxide, and the like. The aminating agent can be used in an equivalent weight of 1 to 20, preferably in an equivalent weight of 1 to 5, with respect to 1 equivalent weight of the compound of the formula (IX-XIII).

The reaction in the production process [P] can be typically carried out in the presence of a solvent and, optionally, in the presence of a copper compound, an organic ligand, and a phase transfer catalyst.

The solvent is not limited to a particular one, provided that the reaction proceeds with use of the solvent. Examples of the solvent include the solvents for use in the first step of the production process [A].

The copper compound is not limited to a particular one, provided that the reaction proceeds with use of the copper compound. Examples of the copper compound include the copper compounds for use in the production process [O]. The copper compound can be used in an equivalent weight of 1 to 20, preferably in an equivalent weight of 1 to 5, with respect to 1 equivalent weight of the compound of the formula (IX-XIII).

The phase transfer catalyst is not limited to a particular one, provided that the reaction proceeds with use of the phase transfer catalyst. Examples of the phase transfer catalyst include the phase transfer catalysts for use in the production process [O]. The phase transfer catalyst can be used in an equivalent weight of 1 to 20, preferably in an equivalent weight of 1 to 5, with respect to 1 equivalent weight of the compound of the formula (IX-XIII).

A reaction temperature is typically 0° C. to 200° C., preferably 0° C. to 120° C. A reaction time is typically 1 hour to 48 hours.

Production Process [Q]

In the production process [Q], a compound represented by a formula (IX-XIV) is caused to react (imination reaction) with an iminating agent to obtain imine, and then the imine is subjected to hydrolysis reaction so as to produce a compound represented by a formula (X-XIV).

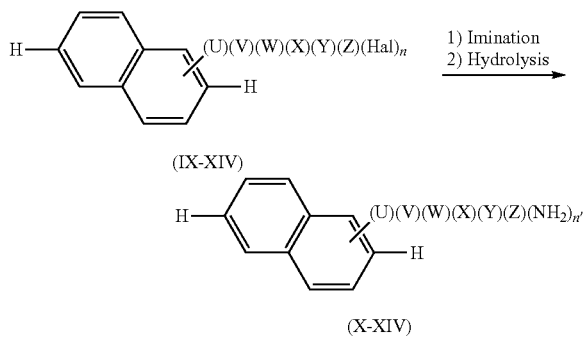

(IX-XIV) → 1) Imination  2) Hydrolysis → (X-XIV)

In the formula (IX-XIV), U, V, W, X, Y, and Z are as described above. Among these substituent groups, at least one substituent group is a halogen atom (Hal), and n represents the number of substituent groups which are halogen atoms (Hal) among the U, V, W, X, Y, and Z and is an integer satisfying $1 \leq n \leq 6$. In the formula (X-XIV), U, V, W, X, Y, and Z are as described above. Among these substituent groups, at least one substituent group is an amino group, and n' is an integer satisfying $1 \leq n' \leq n$.

The iminating agent is not limited to a particular one, provided that the reaction proceeds with use of the iminating agent. Examples of the iminating agent include benzophenone, and the like. The iminating agent can be used in an equivalent weight of 1 to 20, preferably in an equivalent weight of 1 to 5, with respect to 1 equivalent weight of the compound of the formula (IX-XIV).

The imination reaction in the production process [Q] can be carried out typically in the presence of a solvent, a base, and an organic metal catalyst.

The solvent is not limited to a particular one, provided that the reaction proceeds with use of the solvent. Examples of the solvent include the solvents for use in the first step of the production process [A].

The base is not limited to a particular one, provided that the reaction proceeds with use of the base. Examples of the base include the bases for use in the first step of the production process [A]. The base can be used in an equivalent weight of 1 to 20, preferably in an equivalent weight of 1 to 5, with respect to 1 equivalent weight of the compound of the formula (IX-XIV).

The organic metal catalyst is not limited to a particular one, provided that the reaction proceeds with use of the organic metal catalyst. Examples of the organic metal catalyst include the organic metal catalysts for use in the second step of the production process [B]. The organic metal catalyst can be used in an equivalent weight of 0.001 to 5, preferably in an equivalent weight of 0.01 to 1, with respect to 1 equivalent weight of the compound of the formula (IX-XIV).

The hydrolysis reaction in the production process [Q] can be carried out, typically, in the presence of a solvent and acid.

The solvent is not limited to a particular one, provided that the reaction proceeds with use of the solvent. Examples of the solvent include the solvents for use in the first step of the production process [A].

The acid is not limited to a particular one, provided that the reaction proceeds with use of the acid. Examples of the acid include inorganic acids such as hydrochloric acid and sulfuric acid; organic acids such as acetic acid; and the like.

A reaction temperature is typically 0° C. to 200° C., preferably 0° C. to 120° C. A reaction time is typically 1 hour to 48 hours.

Production Process [R]

In the production process [R], a compound represented by a formula (IX-XV) is caused to react (reduction reaction) with metal or metal salt so as to produce a compound represented by a formula (X-XV).

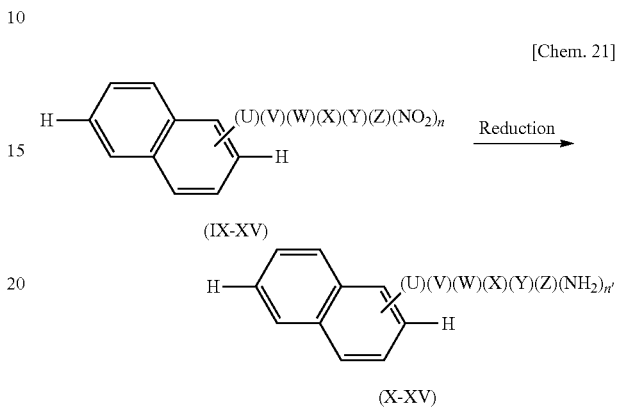

(IX-XV) → Reduction → (X-XV)

In the formula (IX-XV), U, V, W, X, Y, and Z are as described above. Among these substituent groups, at least one substituent group is a nitro group, and n represents the number of substituent groups which are nitro groups among the U, V, W, X, Y, and Z and is an integer satisfying $1 \leq n \leq 6$. In the formula (X-XV), U, V, W, X, Y, and Z are as described above. Among these substituent groups, at least one substituent group is an amino group, and n' is an integer satisfying $1 \leq n' \leq n$.

The metal is not limited to a particular one, provided that the reaction proceeds with use of the metal. Examples of the metal include iron, zinc, tin, and the like. The metal can be used in an equivalent weight of 1 to 20, preferably in an equivalent weight of 1 to 5, with respect to 1 equivalent weight of the compound of the formula (IX-XV).

The metal salt is not limited to a particular one, provided that the reaction proceeds with use of the metal salt. Examples of the metal salt include tin chloride, and the like. The base can be used in an equivalent weight of 1 to 20, preferably in an equivalent weight of 1 to 5, with respect to 1 equivalent weight of the compound of the formula (IX-XV).

The reaction in the production process [R] can be typically carried out in the presence of acid and, optionally, in the presence of a solvent.

The acid is not limited to a particular one, provided that the reaction proceeds with use of the acid. Examples of the acid include the acids for use in the hydrolysis reaction in the production process [Q].

The solvent is not limited to a particular one, provided that the reaction proceeds with use of the solvent. Examples of the solvent include ethers such as tetrahydrofuran, ethylene glycol dimethyl ether, and 1,4-dioxane; esters such as methyl acetate and ethyl acetate; water; and the like. It is possible to select one of or two or more (mixed solvent) of these as appropriate.

A reaction temperature is typically −20° C. to 200° C. A reaction time is typically 1 hour to 48 hours.

Production Process [S]

In the production process [S], a compound represented by a formula (IX-XVI) is caused to react (catalytic reduction reaction) with hydrogen gas or hydrazine so as to produce a compound represented by a formula (X-XVI).

[Chem. 22]

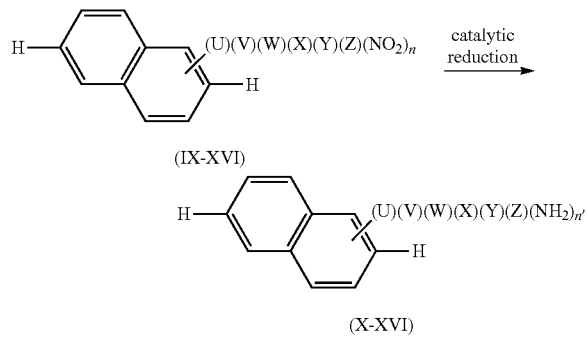

(IX-XVI)

(X-XVI)

In the formula (IX-XVI), U, V, W, X, Y, and Z are as described above. Among these substituent groups, at least one substituent group is a nitro group, and n represents the number of substituent groups which are nitro groups among the U, V, W, X, Y, and Z and is an integer satisfying $1 \leq n \leq 6$. In the formula (X-XVI), U, V, W, X, Y, and Z are as described above. Among these substituent groups, at least one substituent group is an amino group, and n' is an integer satisfying $1 \leq n' \leq n$.

In a case where the hydrogen gas is used as a reducing agent, pressure of the hydrogen gas is not particularly limited, and pressurization can be optionally carried out. The pressure of the hydrogen gas can be typically selected from a range between 0.1 MPa (atmospheric pressure) and 1 MPa, preferably from a range between 0.1 MPa and 0.5 MPa, as appropriate.

In a case where hydrazine is used as a reducing agent, hydrazine can be typically used in an equivalent weight of 1 to 25, with respect to 1 equivalent weight of the compound of the formula (IX-XVI).

The reaction in the production process [S] can be carried out, typically, in the presence of a metal catalyst and a solvent.

The metal catalyst is not limited to a particular one, provided that the reaction proceeds with use of the metal catalyst. Examples of the metal catalyst include palladium catalysts such as palladium black and palladium-supported carbon; platinum catalysts such as platinum-supported carbon and platinum(IV) oxide hydrate; nickel catalysts such as Raney nickel; ruthenium catalysts such as ruthenium-supported carbon; rhodium catalysts such as rhodium-supported carbon; osmium catalysts such as osmium-supported carbon; and the like. The metal catalyst can be used typically in an equivalent weight of 0.0001 to 5, with respect to 1 equivalent weight of the compound of the formula (IX-XVI).

The solvent is not limited to a particular one, provided that the reaction proceeds with use of the solvent. Examples of the solvent include the solvents for use in the first step of the production process [A].

A reaction temperature is typically 20° C. to 100° C., preferably 40° C. to 80° C. A reaction time is typically 1 hour to 48 hours.

With respect to the introduced amino group, it is possible to optionally carry out introduction of a protective group and cleavage (deprotection reaction) of a protective group. A protective group suitable for protection of an amino group, a method for introducing the protective group, and a method for cleaving the protective group are known to a person skilled in the art (for example, see Protective Groups in Organic Synthesis, fourth edition, 2006, John Wiley & Sons, INC.)

The protective group for the amino group encompasses all groups which can be used as protective groups for ordinary amino groups. Specific examples of such groups include groups described in Protective Groups in Organic Synthesis, fourth edition, 2006, John Wiley & Sons, INC., and the like. Specific examples of the protective group include the protective groups for use in the production process [O].

By selecting and combining the production processes [D] through [5] encompassed in the production process [C] as appropriate, it is possible to produce the compound of the formula (II), the formula (III), the formula (IV), or the formula (VIII), which is a substance to be obtained, from the compound of the formula (IX) which is the starting material. Note that the compound of the formula (VIII) can be produced also by causing the compound of the formula (V), the formula (VI), the formula (VII), or the formula (I-I) to react (reduction reaction) with a reducing agent. The reducing agent is not limited to a particular one, provided that the reaction proceeds with use of the reducing agent. Examples of the reducing agent include the reducing agents for use in the second step of the production process [A]. The reducing agent can be used in an equivalent weight of 1 to 20, preferably in an equivalent weight of 1 to 5, with respect to 1 equivalent weight of the compound represented by the formula (V), the formula (VI), the formula (VII), or the formula (I-I).

Production Process [T]

In the production process [T], the compound represented by the formula (V), the formula (VI), the formula (VII), or the formula (I-I) is caused to react (reduction reaction) with metal or metal salt so as to produce the compound represented by the formula (VIII).

[Chem. 23]

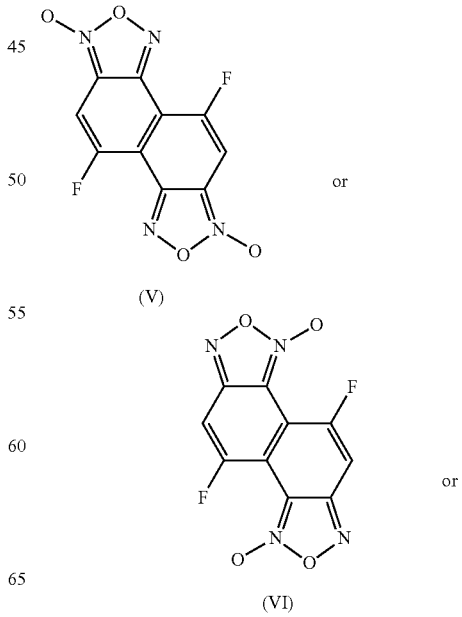

-continued

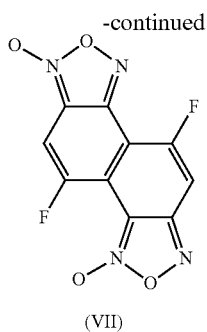

(VII)

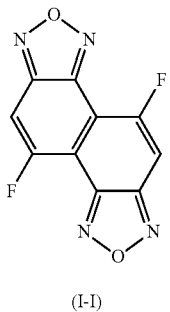

(I-I)

Reduction →

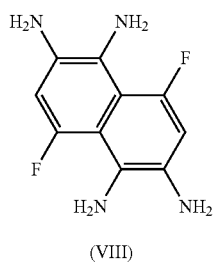

(VIII)

The metal is not limited to a particular one, provided that the reaction proceeds with use of the metal. Examples of the metal include metals for use in the production process [R]. The metal can be used in an equivalent weight of 1 to 20, preferably in an equivalent weight of 1 to 5, with respect to 1 equivalent weight of the compound represented by the formula (V), the formula (VI), the formula (VII), or the formula (I-I).

The metal salt is not limited to a particular one, provided that the reaction proceeds with use of the metal salt. Examples of the metal salt include tin chloride, and the like. The metal salt can be used in an equivalent weight of 1 to 20, preferably in an equivalent weight of 1 to 5, with respect to 1 equivalent weight of the compound represented by the formula (V), the formula (VI), the formula (VII), or the formula (I-I).

The reaction in the production process [T] can be typically carried out in the presence of acid and, optionally, in the presence of a solvent.

The acid is not limited to a particular one, provided that the reaction proceeds with use of the acid. Examples of the acid include the acids for use in the hydrolysis reaction in the production process [Q].

The solvent is not limited to a particular one, provided that the reaction proceeds with use of the solvent. Examples of the solvent include the solvents for use in the production process [R].

A reaction temperature is typically −20° C. to 200° C. A reaction time is typically 1 hour to 48 hours.

Production Process [U]

In the production process [U], the compound represented by the formula (V), the formula (VI), the formula (VII), or the formula (I-I) is caused to react (catalytic reduction reaction) with hydrogen gas or hydrazine so as to produce the compound represented by the formula (VIII).

[Chem. 24]

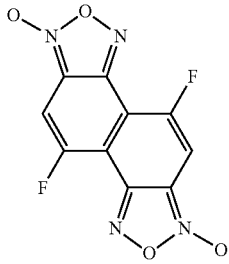

(V)

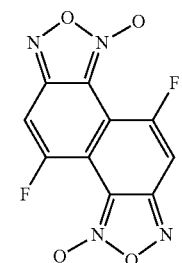

(VI)

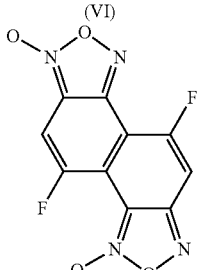

(VII)

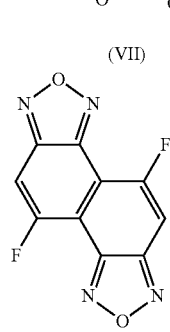

(I-I)

catalytic reduction →

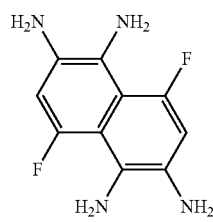

(VIII)

In a case where the hydrogen gas is used as a reducing agent, pressure of the hydrogen gas is not particularly limited, and pressurization can be optionally carried out. The pressure of the hydrogen gas can be typically selected from a range between 0.1 MPa (atmospheric pressure) and 1 MPa, preferably from a range between 0.1 MPa and 0.5 MPa, as appropriate.

In a case where hydrazine is used as a reducing agent, hydrazine can be typically used in an equivalent weight of 1 to 25, with respect to 1 equivalent weight of the compound of the formula (V), the formula (VI), the formula (VII), or the formula (I-I).

The reaction in the production process [U] can be carried out, typically, in the presence of a metal catalyst and a solvent.

The metal catalyst is not limited to a particular one, provided that the reaction proceeds with use of the metal catalyst. Examples of the metal catalyst include the metal catalysts for use in the production process [S]. The metal catalyst can be used typically in an equivalent weight of 0.0001 to 5, with respect to 1 equivalent weight of the compound of the formula (V), the formula (VI), the formula (VII), or the formula (I-I).

The solvent is not limited to a particular one, provided that the reaction proceeds with use of the solvent. Examples of the solvent include the solvents for use in the first step of the production process [A].

A reaction temperature is typically 20° C. to 100° C. A reaction time is typically 1 hour to 48 hours.

[Main Points]

By selecting, combining, and carrying out the production processes [A] through [U] as appropriate, it is possible to produce the naphthobischalcogenadiazole derivative represented by the formula (I), which is a substance to be ultimately obtained, from various starting materials (raw materials) such as, for example, the compound represented by the formula (IX). Specifically, the naphthobischalcogenadiazole derivative represented by the formula (I) can be produced by (i) producing the compound of the formula (II), the formula (III), the formula (IV), or the formula (VIII) from various starting materials such as the compound of the formula (IX) by selecting, combining, and carrying out the production processes [D] through [S] encompassed in the production processes [C] as appropriate and then (ii) selecting, combining, and carrying out the production process [A], the production process [B], the production process [T], and the production process [U], as appropriate.

Specifically, it is preferable to produce the naphthobischalcogenadiazole derivative by carrying out the following steps.

(1) Producing difluoronaphthalene by subjecting diaminonaphthalene to fluorination reaction.

(2) Producing diamino-difluoronaphthalene or hydrochloride thereof by subjecting the difluoronaphthalene to amination reaction.

(3) Producing diamino-difluoro-dinitronaphthalene or hydrochloride thereof by subjecting the diamino-difluoronaphthalene or hydrochloride thereof to nitration reaction.

(4) Producing tetraamino-difluoronaphthalene or hydrochloride thereof by reducing the diamino-difluoro-dinitronaphthalene or hydrochloride thereof.

(5) Producing a naphthobischalcogenadiazole derivative represented by the formula (I) (where $X^1$ and $X^2$ are hydrogen atoms) by subjecting the tetraamino-difluoronaphthalene or hydrochloride thereof to react with a sulfurizing agent, a selenizing agent, or a tellurizing agent.

(6) Producing a naphthobischalcogenadiazole derivative represented by the formula (I) (where $X^1$ and $X^2$ are the forgoing substances excluding hydrogen atoms) by causing the naphthobischalcogenadiazole derivative obtained in the step (5) to react with a halogenating agent or a boronizing agent.

As an alternative method, it is preferable to produce a naphthobischalcogenadiazole derivative represented by the formula (I) (where $A^1$ and $A^2$ are oxygen atoms) by specifically carrying out the following steps.

(7) Producing a naphthobischalcogenadiazole derivative represented by the formula (I) (where $X^1$ and $X^2$ are hydrogen atoms and $A^1$ and $A^2$ are oxygen atoms) by oxidizing and then reducing the diamino-difluoro-dinitronaphthalene or hydrochloride thereof obtained in the step (3).

(8) Producing a naphthobischalcogenadiazole derivative represented by the formula (I) (where $X^1$ and $X^2$ are the foregoing substances excluding hydrogen atoms, and $A^1$ and $A^2$ are oxygen atoms) by causing the naphthobischalcogenadiazole derivative obtained in the step (7) to react with a halogenating agent or a boronizing agent.

A person skilled in the art can easily consider and understand, from the descriptions in this specification, (i) a specific structure of a compound to be selected as, for example, the compound of the formula (IX) which is a starting material, (ii) necessary reaction to be selected for introducing an amino group, a nitro group, a fluoro group, and the like into the selected compound, (iii) how to combine and carry out the selected reactions (synthetic pathway), (iv) and the like. Therefore, the method for producing the naphthobischalcogenadiazole derivative represented by the formula (I) by appropriately selecting, combining, and carrying out the production processes [A] through [U] is also clearly encompassed in the scope of the present invention.

The present invention is not limited to the embodiments described above, but may be altered in various ways by a skilled person within the scope of the claims. Any embodiment based on a proper combination of technical means disclosed in different embodiments is also encompassed in the technical scope of the present invention. Further, by combining technical means disclosed in different embodiments, it is possible to obtain a new technical feature.

EXAMPLES

The present invention will be described below in more detail with reference to Examples. Note, however, that the present invention is not limited to such Examples. Note that, in the present invention, the "room temperature" indicates a temperature of 25±15° C.

<Conditions for Measuring Physical Properties, Etc.>

A nuclear magnetic resonance (NMR) spectrum was measured with use of "JMM-ECS400 (product name)" manufactured by JEOL Ltd., "JNM-ECA600 (product name)" manufactured by JEOL Ltd., "ECX (500 MHz) (product name)" manufactured by JEOL Ltd., or "AVANCEIII700 (product name)" manufactured by Bruker BioSpin K.K. A chemical shift is indicated in parts per million (ppm). As an internal standard (0 ppm), tetramethylsilane (TMS) was used. A coupling constant (J) is indicated in hertz, and abbreviations s, d, t, q, m, and br represent singlet, doublet, triplet, quartet, multiplet, and broad, respectively.

Mass spectroscopy (MS) is carried out by a direct insertion (DI) method with use of "GCMS-QP5050A (product name)" manufactured by Shimadzu Corporation.

All chemical substances used in Examples and silica gel in column chromatographic separation were of reagent grade, and were purchased from Wako Pure Chemical Indus-

Example 1

Synthesis of 5,10-difluoronaphtho[1,2-c:5,6-c']bis[1,2,5]thiadiazol

As indicated in the following reaction formula, 1,2,5,6-tetraamino-4,8-difluoronaphthalene which was a compound represented by the formula (VIII) was obtained from a compound represented by the formula (IX) by (i) producing the compound of the formula (IX) from commercially available naphthalene by appropriately selecting, combining, and carrying out the production processes such as nitration, halogenation, boronization, hydroxylation, and amination, and then (ii) appropriately selecting, combining, and carrying out the production processes [A] through [U].

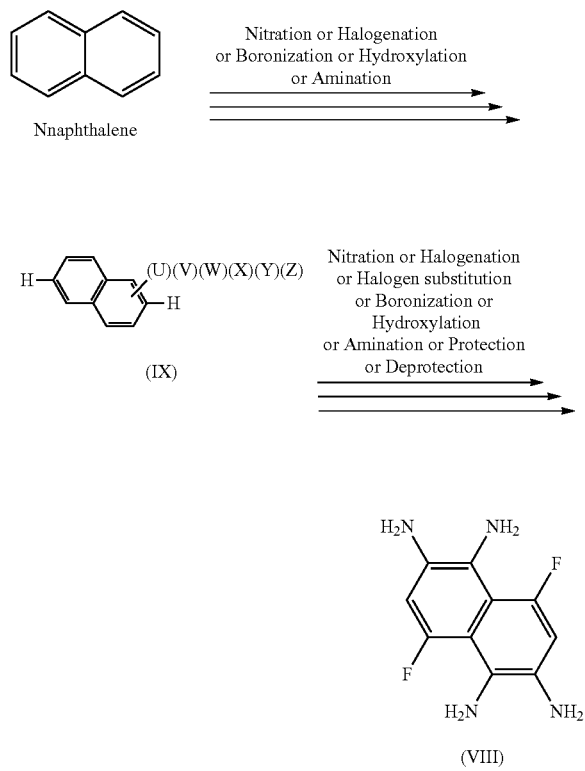

The obtained 1,2,5,6-tetraamino-4,8-difluoronaphthalene (174 mg), pyridine (18 mL), and thionyl chloride (1.12 g) were put into a 100-mL eggplant-shaped flask, and stirred for 2 hours at 90° C. Then, the reaction liquid was dried under reduced pressure to obtain a solid substance. To the obtained solid substance, methyl alcohol was added and the mixture was filtered, and then a solid substance taken by the filtration was cleaned with methyl alcohol. The cleaned solid substance was dried, and thus a brown and solid objective substance (130 mg, 99%) was obtained. The following indicates the reaction formula.

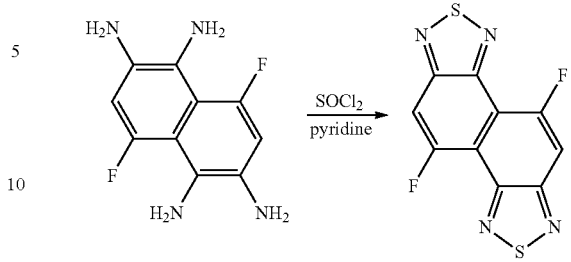

Physical properties of the obtained objective substance were measured. Measurement results are as follows:

$^1$H-NMR (400 MHz, CDCl$_3$): δ=8.08-8.03 (m, 2H). $^{19}$F-NMR (565 MHz, CDCl$_3$): δ=−107.71.

From the measurement results, it was confirmed that the objective substance was 5,10-difluoronaphtho[1,2-c:5,6-c']bis[1,2,5]thiadiazol.

Example 2

Synthesis of 5,10-difluoronaphtho[1,2-c:5,6-c']bis[1,2,5]thiadiazol

Synthesis of 1,5-difluoronaphthalene 1,5-diaminonaphthalene (7.5 g) and water (200 mL) were put into a 500-mL eggplant-shaped flask and cooled to 0° C., and then concentrated sulfuric acid (12.6 mL) was put into the flask. Then, an aqueous solution (20 mL) of nitrous acid (8.21 g) was dripped at 0° C. and, after the dripping was finished, the mixture was stirred for 1 hour at 0° C. After that, the mixture was stirred for 1 hour at the room temperature. Then, the mixture was cooled to 0° C. and HBF$_4$ (38 mL) was dripped and, after the dripping was finished, the mixture was stirred for 1 hour at 0° C. The precipitate was taken by filtration and cleaned with water and methanol, and dried under reduced pressure to obtain a solid substance. The obtained solid substance (17.6 g) and chlorobenzene (150 mL) where put into a 500-mL eggplant-shaped flask, and were heated to reflux for 3 hours. Then, water was added to the reaction liquid which had been cooled to 0° C., and extraction was carried out with use of chloroform, an organic layer was dried with use of anhydrous sodium sulfate, and the solvent after filtration was evaporated under reduced pressure. The reaction mixture thus obtained was separated and refined by silica gel column chromatography in which hexane was used as a mobile phase, and thus white and solid 1,5-difluoronaphthalene was obtained (3.048 g, yield of 39%). The following indicates the reaction formula.

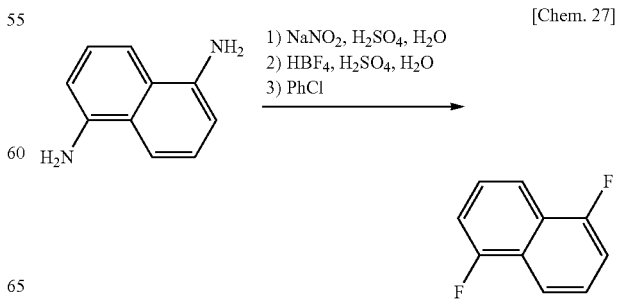

Physical properties of the obtained objective substance were measured. Measurement results are as follows:

¹H-NMR (400 MHz, CDCl₃): δ=7.88 (d, J=8.4 Hz, 1H), 7.49-7.44 (m, 1H), 7.21 (dd, J=7.8 Hz, 11 Hz, 1H).

Synthesis of 1,5-dibromo-4,8-difluoronaphthalene 1,5-difluoronaphthalene (3.048 g) and trifluoroacetic acid (25 mL) were put into a 200-mL eggplant-shaped flask, and then N-bromosuccinimide (7.939 g) was added and stirred for 16 hours at 70° C. Then, water was added to the reaction liquid which had been cooled to 0° C., the obtained precipitate was taken by filtration, and was cleaned with water and methanol. Then, the cleaned substance was dried under reduced pressure, and thus pale brown and solid 1,5-dibromo-4,8-difluoronaphthalene was obtained (5.321 g, yield of 89%). The following indicates the reaction formula.

[Chem. 28]

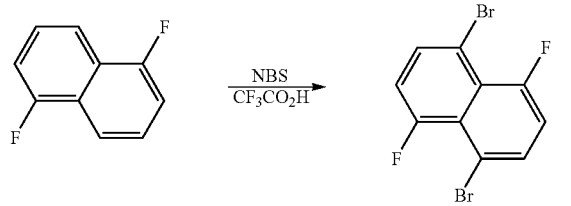

Physical properties of the obtained objective substance were measured. Measurement results are as follows:

¹H-NMR (400 MHz, CDCl₃): δ=7.88 (dd, J=4.2 Hz, 8.6 Hz, 2H), 7.12 (dd, J=8.6 Hz, 12.6 Hz, 2H).

Synthesis of 1,5-diamino-4,8-difluoronaphthalene Hydrochloride 1,5-dibromo-4,8-difluoronaphthalene (5.00 g), a tris(dibenzylideneacetone)dipalladium(0)-chloroform adduct (802 mg), rac-2,2'-bis(diphenylphosphino)1,1'-binaphthyl (483 mg), sodium tert-butoxide (5.96 g), benzophenone imine (802 mg), and toluene (80 mL) were put into a 300-mL eggplant-shaped flask, and the air inside the flask was replaced with nitrogen, and the mixture was stirred for 16 hours at 110° C. The precipitate was taken by Celite filtration and cleaned with ethyl acetate, and the filtrate was evaporated under reduced pressure. The reaction mixture thus obtained was separated and refined by silica gel column chromatography in which a solvent containing hexane:ethyl acetate (1:1) was used as a mobile phase. The reaction product thus obtained and THF (115 mL) were put into a 300-mL eggplant-shaped flask, and 2N hydrochloric acid (23.5 mL) was added at 0° C., and the mixture was stirred for 1 hour at 0° C. The precipitate was taken by filtration and cleaned with tetrahydrofuran. Then, the cleaned substance was dried under reduced pressure, and thus pale brown and solid 1,5-diamino-4,8-difluoronaphthalene hydrochloride was obtained (2.00 g, yield of 48%). The following indicates the reaction formula. In the formula, n is an arbitrary numeral of 0 to 4.

[Chem. 29]

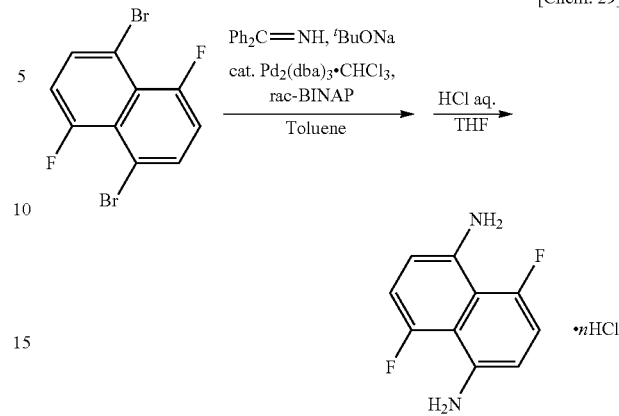

Physical properties of the obtained objective substance were measured. Measurement results are as follows:

¹H-NMR (400 MHz, DMSO-d₆): δ=7.30-7.25 (m, 4H).

(Synthesis of N,N'-(4,8-difluoronaphthalene-1,5-diyl)bis(2,2,2-trifluoroacetamide))

1,5-diamino-4,8-difluoronaphthalene hydrochloride (1.95 g) and dichloromethane (85 mL) were put into a 300-mL eggplant-shaped flask and cooled to 0° C. Triethylamine (2.95 g) and trifluoroacetic anhydride (7.67 g) were added at 0° C., and stirred all night at the room temperature. The reaction mixture thus obtained was dried under reduced pressure. To the precipitate, methanol was added, and the precipitate was then taken by filtration and was cleaned with methanol. After that, the cleaned substance was dried under reduced pressure, and thus white and solid N,N'-(4,8-difluoronaphthalene-1,5-diyl)bis(2,2,2-trifluoroacetamide was obtained (2.410 g, yield of 86%). The following indicates the reaction formula.

[Chem. 30]

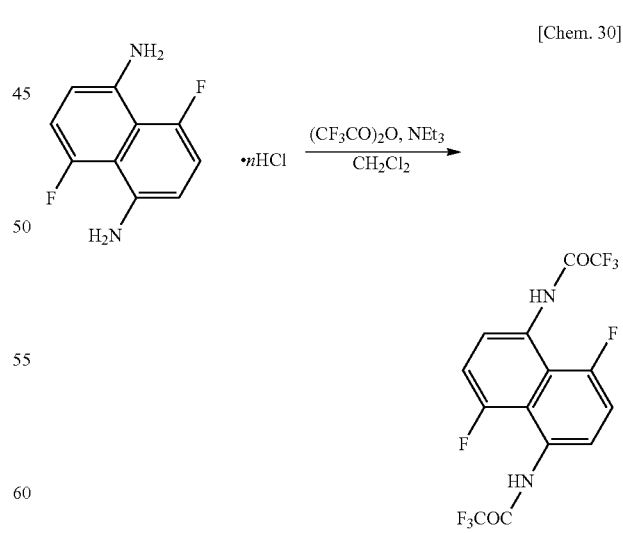

Physical properties of the obtained objective substance were measured. Measurement results are as follows:

¹H-NMR (400 MHz, Acetone-d₆): δ=10.43 (br, 2H), 7.84-7.79 (m, 2H), 7.50 (dd, J=8.4 Hz, 13.6 Hz, 2H).

(Synthesis of N,N'-(4,8-difluoro-2,6-dinitronaphtha-lene-1,5-diyl)bis(2,2,2-trifluoroacetamide))

N,N'-(4,8-difluoronaphthalene-1,5-diyl)bis(2,2,2-trifluoroacetamide) (500 mg) and concentrated sulfuric acid (10 mL) were put into a 50-mL eggplant-shaped flask, and cooled to −45° C. After that, nitric acid (2.5 mL) was added, and stirred for 5 minutes at −45° C. The reaction mixture thus obtained was added to ice water, extraction was carried out with ethyl acetate, and an organic layer was cleaned with water. The organic layer was dried with use of anhydrous sodium sulfate, and the solvent after filtration was evaporated under reduced pressure. Diethyl ether was added to the precipitated solid substance, and the precipitated solid substance was taken by filtration and cleaned with diethyl ether. After that, the cleaned substance was dried under reduced pressure, and thus pale brown and solid N,N'-(4,8-difluoro-2,6-dinitronaphthalene-1,5-diyl)bis(2,2,2-trifluoroacetamide) was obtained (313 mg, yield of 51%). The following indicates the reaction formula.

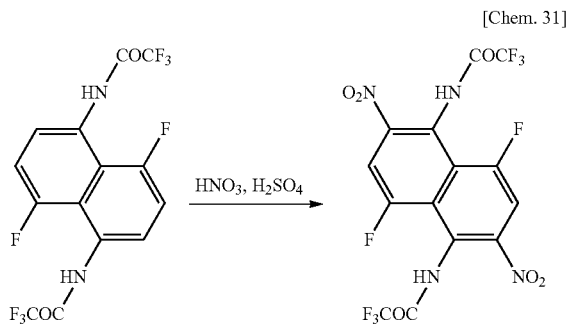

[Chem. 31]

Physical properties of the obtained objective substance were measured. Measurement results are as follows:

$^1$H-NMR (400 MHz, Acetone-d$_6$): δ=11.00 (br, 2H), 8.31 (d, J=12.8 Hz, 2H).

Synthesis of 1,5-diamino-4,8-difluoro-2,6-dinitronaphthalene Hydrochloride

N,N'-(4,8-difluoro-2,6-dinitronaphthalene-1,5-diyl)bis(2,2,2-trifluoroacetamide) (1.340 g), methanol (110 mL), and concentrated hydrochloric acid (55 mL) were put into a 300-mL eggplant-shaped flask, and stirred all night at 90° C. The reaction mixture was concentrated under reduced pressure. The precipitated solid substance was taken by filtration, and cleaned with concentrated hydrochloric acid and dichloromethane. Then, the cleaned substance was dried under reduced pressure, and thus dark brown and solid 1,5-diamino-4,8-difluoro-2,6-dinitronaphthalene hydrochloride was obtained (679 mg, yield of 68%). The following indicates the reaction formula. In the formula, n is an arbitrary numeral of 0 to 4.

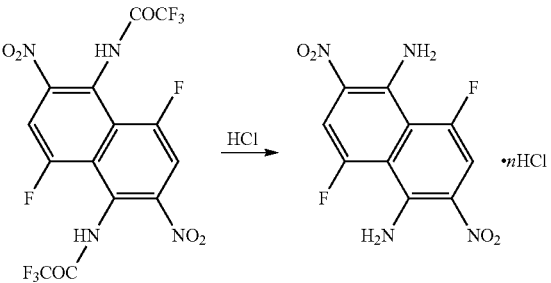

[Chem. 32]

Physical properties of the obtained objective substance were measured. Measurement results are as follows:

$^1$H-NMR (400 MHz, DMSO-d$_6$): δ=8.15 (br, 4H), 7.92 (d, J=16.4 Hz, 2H)

Synthesis of 1,2,5,6-tetraamino-4,8-difluoronaphthalene Hydrochloride 1,5-diamino-4,8-difluoro-2,6-dinitronaphthalene hydrochloride (797 mg), concentrated hydrochloric acid (80 mL), and tin(II) chloride (8.46 g) were put into a 300-mL eggplant-shaped flask, and stirred for 1 hour at 70° C. The precipitated solid substance was taken by filtration, and cleaned with concentrated hydrochloric acid and dichloromethane. Then, the cleaned substance was dried under reduced pressure, and thus brown and solid 1,2,5,6-tetraamino-4,8-difluoronaphthalene hydrochloride was obtained (718 mg, yield of 87%). The following indicates the reaction formula. In the formula, each of m and n is independently an arbitrary numeral of 0 to 4.

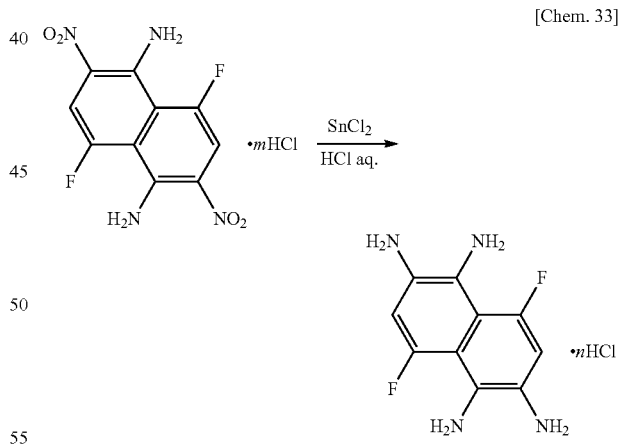

[Chem. 33]

Physical properties of the obtained objective substance were measured. Measurement results are as follows:

$^1$H-NMR (400 MHz, DMSO-d$_6$): δ=6.94 (d, J=16.8 Hz, 2H).

Synthesis of 5,10-difluoronaphtho[1,2-c:5,6-c]bis[1,2,5]thiadiazol

The obtained 1,2,5,6-tetraamino-4,8-difluoronaphthalene hydrochloride (174 mg), pyridine (18 mL), and thionyl chloride (1.12 g) were put into a 100-mL eggplant-shaped flask, and stirred for 2 hours at 90° C. Then, the reaction liquid was dried under reduced pressure to obtain a solid substance. To the obtained solid substance, methyl alcohol was added and the mixture was filtered, and then a solid substance taken by the filtration was cleaned with methyl alcohol. The cleaned solid substance was dried, and thus pale brown 5,10-difluoronaphtho[1,2-c:5,6-c]bis[1,2,5]thiadiazol (130 mg, 99%) was obtained. The following indicates the reaction formula.

[Chem. 34]

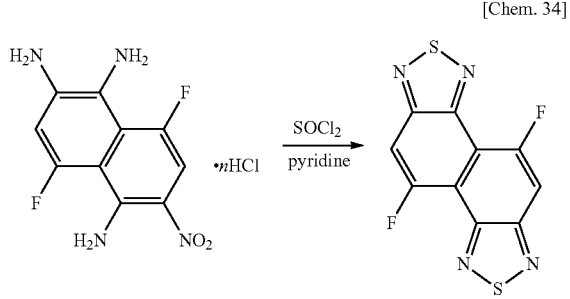 [SMILES: Nc1cc(F)c2c(N)c([N+](=O)[O-])cc(F)c2c1N ; "SOCl2" ; "pyridine" ; Fc1cc2nsnc2c2c(F)cc3nsnc3c12]

Physical properties of the obtained objective substance were measured. Measurement results are as follows:

$^1$H-NMR (400 MHz, CDCl$_3$): δ=8.08-8.03 (m, 2H). $^{19}$F-NMR (565 MHz, CDCl$_3$): δ=−107.71.

From the measurement results, it was confirmed that the objective substance was 5,10-difluoronaphtho[1,2-c:5,6-c]bis[1,2,5]thiadiazol.

Example 3

Synthesis of 5,10-difluoronaphtho[1,2-c:5,6-c]bis[1,2,5]selenadiazole

In a manner similar to that of Example 1, 1,2,5,6-tetraamino-4,8-difluoronaphthalene was obtained.

Next, the obtained 1,2,5,6-tetraamino-4,8-difluoronaphthalene hydrochloride (90 mg), pyridine (9 mL), and selenium oxychloride (806 mg) were put into a 50-mL eggplant-shaped flask, and stirred for 2 hours at 90° C. Then, the reaction liquid was dried under reduced pressure to obtain a solid substance. To the obtained solid substance, methyl alcohol was added and the mixture was filtered, and then a solid substance taken by the filtration was cleaned with methyl alcohol. The cleaned solid substance was dried, and thus a brown and solid objective substance (110 mg, 99%) was obtained. The following indicates the reaction formula.

[Chem. 35]

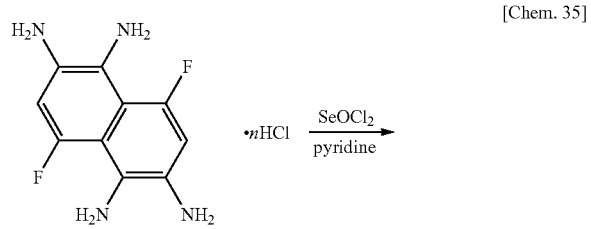

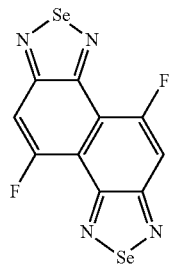

Physical properties of the obtained objective substance were measured. Measurement results are as follows:

$^1$H-NMR (400 MHz, CF$_3$CO$_2$D): δ=8.08 (d, J=12.0 Hz, 2H). MS (DI) m/z=376.

From the measurement results, it was confirmed that the objective substance was 5,10-difluoronaphtho[1,2-c:5,6-c]bis[1,2,5]selenadiazole.

Example 4

Synthesis of 4,9-dibromo-5,10-difluoronaphtho[1,2-c:5,6-c]bis[1,2,5]thiadiazol

The 5,10-difluoronaphtho[1,2-c:5,6-c']bis[1,2,5]thiadiazol (30 mg) obtained in Example 1, concentrated sulfuric acid (3.2 g), and N-bromosuccinimide (77 mg) were put into a 20-mL eggplant-shaped flask, and stirred for 2 hours at 60° C. Further, N-bromosuccinimide (77 mg) was added, and the mixture was stirred for 2 hours at 60° C. After that, the reaction liquid was quenched in ice water, and extraction was carried out with use of chloroform. The extraction liquid was cleaned with a saturated aqueous sodium hydrogencarbonate solution, and then the extraction liquid was concentrated under reduced pressure. To the obtained solid substance, methyl alcohol was added and the mixture was filtered, and then a solid substance taken by the filtration was cleaned with methyl alcohol. The cleaned solid substance was dried, and thus a yellow and solid objective substance (24 mg, 51%) was obtained. The following indicates the reaction formula.

[Chem. 36]

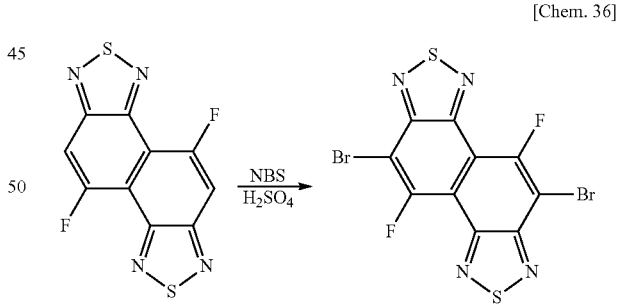

Physical properties of the obtained objective substance were measured. Measurement results are as follows:

$^{19}$F-NMR (470 MHz, CDCl$_3$): δ=−99.9 (s). Melting point (m.p.)=270° C. to 272° C.

Example 5

Synthesis of 4,9-dibromo-5,10-difluoronaphtho[1,2-c:5,6-c]bis[1,2,5]thiadiazol

The 5,10-difluoronaphtho[1,2-c:5,6-c']bis[1,2,5]thiadiazol (90 mg, 0.32 mmol) obtained in Example 1, trifluoroacetic acid (20 mL), and N-bromosuccinimide (77 mg) were put into a reactor vessel, and stirred for 20 hours at 70° C. After that, water was added to the reaction solution, and the precipitated yellow solid substance was filtered out, cleaned with methanol, and dried. Thus an objective substance was obtained (100 mg, 72%).

Physical properties of the obtained objective substance were measured. Measurement results are as follows:

$^{19}$F-NMR (470 MHz, CDCl$_3$): δ=−99.9 (s). Melting point (m.p.)=270° C. to 272° C.

INDUSTRIAL APPLICABILITY

According to the present invention, it is possible to provide the naphthobischalcogenadiazole derivative into which a fluorine atom has been introduced and which is useful as an intermediate of an organic semiconductor material that excels in electron-accepting property. The naphthobischalcogenadiazole derivative can be used as a production intermediate having high versatility for producing a naphthobischalcogenadiazole compound into which a fluorine atom has been introduced, which is a substituent group having a strong electron-withdrawing property for improving an electron-accepting property.

The invention claimed is:

1. A naphthobischalcogenadiazole derivative represented by a formula (I):

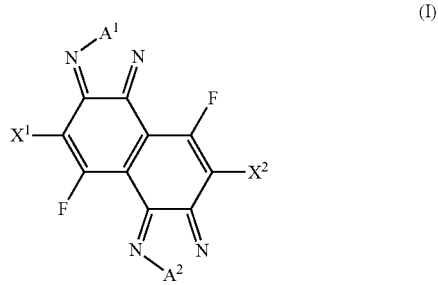

(I)

where each of A$^1$ and A$^2$ is independently an oxygen atom, a sulfur atom, a selenium atom, or a tellurium atom; and each of X$^1$ and X$^2$ is independently a boronic acid group, a boronic acid ester group, a boronic acid diaminonaphthalene amide group, an N-methyliminodiacetic acid boronate group, a trifluoroborate salt group, or a triolborate salt group.

2. The naphthobischalcogenadiazole derivative as set forth in claim 1, wherein each of A$^1$ and A$^2$ is independently an oxygen atom, a sulfur atom, or a selenium atom.

3. The naphthobischalcogenadiazole derivative as set forth in claim 1, wherein both of A$^1$ and A$^2$ are sulfur atoms or selenium atoms.

4. The naphthobischalcogenadiazole derivative as set forth in claim 1, wherein both of X$^1$ and X$^2$ are boronic acid ester groups.

5. The naphthobischalcogenadiazole derivative as set forth in claim 4, wherein the boronic acid ester group is a boronic acid dialkyl ester group or a boronic acid cyclic ester group.

6. A method for producing a naphthobischalcogenadiazole derivative represented by a formula (I):

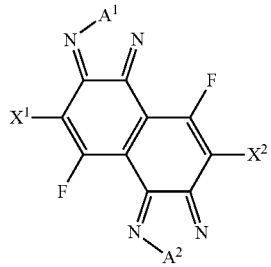

(I)

where each of A$^1$ and A$^2$ is independently an oxygen atom, a sulfur atom, a selenium atom, or a tellurium atom; and each of X$^1$ and X$^2$ is independently a hydrogen atom, a halogen atom, a boronic acid group, a boronic acid ester group, a boronic acid diaminonaphthalene amide group, an N-methyliminodiacetic acid boronate group, a trifluoroborate salt group, or a triolborate salt group, said method comprising the step of oxidizing and then reducing diamino-difluoro-dinitronaphthalene or hydrochloride thereof.

7. A method as set forth in claim 6, said method comprising the steps of:
reducing the diamino-difluoro-dinitronaphthalene or hydrochloride thereof to obtain tetraamino-difluoronaphthalene or hydrochloride thereof;
causing the tetraamino-difluoronaphthalene or hydrochloride thereof to react with a sulfurizing agent, a selenizing agent, or a tellurizing agent to obtain a naphthobischalcogenadiazole derivative; and then
causing the naphthobischalcogenadiazole derivative to react with a halogenating agent or a boronizing agent.

8. A method as set forth in claim 6, said method comprising the steps of oxidizing and then reducing diamino-difluoro-dinitronaphthalene or hydrochloride thereof, and causing a naphthobischalcogenadiazole derivative, which has been obtained in the above step, to react with a halogenating agent or a boronizing agent.

9. A method as set forth in claim 6, further comprising the steps of:
producing tetraamino-difluoronaphthalene or hydrochloride thereof by reducing the diamino-difluoro-dinitronaphthalene or hydrochloride thereof; and then
causing the tetraamino-difluoronaphthalene or hydrochloride thereof to react with a sulfurizing agent, a selenizing agent, or a tellurizing agent.

10. A method as set forth in claim 6, further comprising the step of producing the diamino-difluoro-dinitronaphthalene or hydrochloride thereof by subjecting diamino-difluoronaphthalene or hydrochloride thereof to nitration reaction.

11. A method as set forth in claim 10, further comprising the step of producing the diamino-difluoronaphthalene or hydrochloride thereof by subjecting difluoronaphthalene to amination reaction.

12. A method as set forth in claim 11, further comprising the step of producing the difluoronaphthalene by subjecting diaminonaphthalene to fluorination reaction.

13. A method as set forth in claim 9, further comprising the step of producing the diamino-difluoro-dinitronaphthalene or hydrochloride thereof by subjecting diamino-difluoronaphthalene or hydrochloride thereof to nitration reaction.

14. A method as set forth in claim 13, further comprising the step of producing the diamino-difluoronaphthalene or hydrochloride thereof by subjecting difluoronaphthalene to amination reaction.

15. A method as set forth in claim 14, further comprising the step of producing the difluoronaphthalene by subjecting diaminonaphthalene to fluorination reaction.

* * * * *